US011529600B2

(12) United States Patent
Vogt et al.

(10) Patent No.: US 11,529,600 B2
(45) Date of Patent: Dec. 20, 2022

(54) POWDER-LIQUID BONE CEMENT MIXER WITH COMPRESSED GAS CONNECTION

(71) Applicant: Heraeus Medical GmbH, Wehrheim (DE)

(72) Inventors: Sebastian Vogt, Erfurt (DE); Thomas Kluge, Vallendar (DE)

(73) Assignee: Heraeus Medical GmbH, Wehrheim (DE)

( * ) Notice: Subject to any disclaimer, the term of this patent is extended or adjusted under 35 U.S.C. 154(b) by 875 days.

(21) Appl. No.: 16/178,188

(22) Filed: Nov. 1, 2018

(65) Prior Publication Data

US 2019/0126224 A1    May 2, 2019

(30) Foreign Application Priority Data

Nov. 2, 2017    (DE) .......................... 102017125592.3

(51) Int. Cl.
 *B01F 35/75*    (2022.01)
 *A61L 24/06*    (2006.01)
 (Continued)

(52) U.S. Cl.
 CPC ...... *B01F 35/7543* (2022.01); *A61B 17/8833* (2013.01); *A61L 24/06* (2013.01);
 (Continued)

(58) Field of Classification Search
 CPC .... B01F 35/7543; B01F 23/54; B01F 35/189; B01F 35/7131; B01F 35/7161;
 (Continued)

(56) References Cited

U.S. PATENT DOCUMENTS

| 2,446,501 A | 8/1948 | Weber |
| 3,739,947 A | 6/1973 | Baumann et al. |

(Continued)

FOREIGN PATENT DOCUMENTS

| DE | 3640279 A1 | 6/1987 |
| DE | 4030832 A1 | 7/1991 |

(Continued)

OTHER PUBLICATIONS

English translation of the office action dated Sep. 30, 2019 by the Japanese Patent Office for counterpart Japanese Patent Application No. 2018-206704.

(Continued)

*Primary Examiner* — Charles Cooley
(74) *Attorney, Agent, or Firm* — Dicke, Billig & Czaja, PLLC

(57) ABSTRACT

A device and method for producing a bone cement paste from a monomer liquid and a cement powder, wherein the device comprises a cartridge with a cylindrical interior chamber for mixing the parent components, whereby the interior chamber of the cartridge is closed on the front side up to a delivery opening for expelling the bone cement paste from the interior chamber, a delivery plunger which is arranged in the interior chamber of the cartridge and which is supported in a linearly movable manner in the direction of the delivery opening, the cement powder, which is arranged in the interior chamber of the cartridge between the delivery opening and the delivery plunger, a monomer receptacle with an interior chamber in which a monomer liquid container containing the monomer liquid is contained, whereby in the monomer receptacle, a conveying plunger is arranged movable in the longitudinal direction of the monomer receptacle, a compressed gas connection, whereby the conveying plunger is arranged between the monomer liquid container (Continued)

and the compressed gas connection or the compressed gas line in the monomer receptacle.

17 Claims, 23 Drawing Sheets

(51) Int. Cl.
*A61B 17/88* (2006.01)
*B01F 23/50* (2022.01)
*B01F 35/00* (2022.01)
*B01F 35/71* (2022.01)
*B01F 101/20* (2022.01)

(52) U.S. Cl.
CPC ............ *B01F 23/54* (2022.01); *B01F 35/189* (2022.01); *B01F 35/7131* (2022.01); *B01F 35/7161* (2022.01); *B01F 35/7164* (2022.01); *B01F 35/7174* (2022.01); *B01F 35/71745* (2022.01); *B01F 35/75425* (2022.01); *B01F 35/754251* (2022.01); *A61L 2430/02* (2013.01); *B01F 23/565* (2022.01); *B01F 2101/20* (2022.01)

(58) Field of Classification Search
CPC .............. B01F 35/7164; B01F 35/7174; B01F 35/71745; B01F 35/75425; B01F 35/754251; B01F 23/565; B01F 2101/20; A61B 17/8833; A61L 24/06; A61L 2430/02
USPC .................................................. 366/139, 191
See application file for complete search history.

(56) References Cited

U.S. PATENT DOCUMENTS

| | | | |
|---|---|---|---|
| 4,671,263 A * | 6/1987 | Draenert ............ | A61B 17/8833 606/94 |
| 4,758,096 A | 7/1988 | Gunnarsson | |
| 4,973,168 A | 11/1990 | Chan | |
| 5,100,241 A | 3/1992 | Chan | |
| 5,193,907 A | 3/1993 | Faccioli et al. | |
| 5,344,232 A | 9/1994 | Nelson et al. | |
| 5,551,778 A | 9/1996 | Hauke et al. | |
| 5,586,821 A | 12/1996 | Bonitati et al. | |
| 5,588,745 A * | 12/1996 | Tanaka ................ | A61B 17/8833 206/222 |
| 5,624,184 A | 4/1997 | Chan | |
| 5,997,544 A | 12/1999 | Nies et al. | |
| 6,033,105 A | 3/2000 | Barker et al. | |
| 6,709,149 B1 | 3/2004 | Tepic | |
| 6,935,541 B1 * | 8/2005 | Campbell ............ | B05C 17/015 137/557 |
| 10,485,598 B2 * | 11/2019 | Vogt ................... | A61B 17/8833 |
| 10,517,661 B2 * | 12/2019 | Vogt ................... | A61B 17/8816 |
| 10,517,662 B2 * | 12/2019 | Vogt ........................ | B01F 33/70 |
| 10,518,232 B2 * | 12/2019 | Vogt ...................... | B01F 35/718 |
| 10,639,088 B2 * | 5/2020 | Vogt .......................... | A61C 5/64 |
| 10,722,855 B2 * | 7/2020 | Vogt ........................ | B01F 23/53 |
| 10,765,463 B2 * | 9/2020 | Vogt ................. | B01F 35/754251 |
| 10,765,464 B2 * | 9/2020 | Kluge .............. | B01F 35/754251 |
| 10,875,000 B2 * | 12/2020 | Vogt .................... | A61B 17/8816 |
| 10,987,147 B2 * | 4/2021 | Vogt .................. | B01F 33/50112 |
| 11,039,872 B2 * | 6/2021 | Vogt .................. | B01F 33/50112 |
| 11,103,295 B2 * | 8/2021 | Vogt ........................ | B01F 23/50 |
| 11,109,905 B2 * | 9/2021 | Vogt .................. | B01F 33/50112 |
| 11,109,906 B2 * | 9/2021 | Vogt ...................... | B01F 35/7131 |
| 11,154,343 B2 * | 10/2021 | Vogt ...................... | A61L 24/043 |
| 11,241,266 B2 * | 2/2022 | Vogt ...................... | B01F 35/7174 |
| 11,291,490 B2 * | 4/2022 | Vogt .................... | A61B 17/8833 |
| 2001/0008968 A1 | 7/2001 | Overes et al. | |
| 2004/0066706 A1 | 4/2004 | Barker et al. | |
| 2004/0074927 A1 | 4/2004 | Lafond | |
| 2010/0329074 A1 | 12/2010 | Vogt et al. | |
| 2011/0056984 A1 | 3/2011 | Cheetham | |
| 2012/0155214 A1 | 6/2012 | Faccioli et al. | |
| 2013/0135957 A1 | 5/2013 | Vogt et al. | |
| 2013/0138113 A1 | 5/2013 | Vogt et al. | |
| 2013/0172896 A1 * | 7/2013 | Vogt .................... | A61B 17/8802 606/94 |
| 2013/0231673 A1 | 9/2013 | Vogt et al. | |
| 2015/0164568 A1 | 6/2015 | Vogt | |
| 2015/0216577 A1 | 8/2015 | Vogt et al. | |
| 2016/0214135 A1 | 7/2016 | Vogt | |
| 2017/0128113 A1 * | 5/2017 | Vogt .................. | B05C 17/00573 |
| 2017/0291153 A1 | 10/2017 | Vogt et al. | |
| 2019/0126224 A1 * | 5/2019 | Vogt .................... | B01F 15/0237 |
| 2022/0175435 A1 * | 6/2022 | Chen ........................ | B01F 23/53 |

FOREIGN PATENT DOCUMENTS

| | | |
|---|---|---|
| DE | 69812726 T2 | 2/2004 |
| DE | 202005010206 U1 | 9/2005 |
| DE | 102009031178 B3 | 9/2010 |
| DE | 102010019220 B4 | 3/2015 |
| DE | 102013226118 B3 | 6/2015 |
| DE | 102014101305 A1 | 8/2015 |
| DE | 102015101126 A1 | 7/2016 |
| EP | 0692229 A1 | 1/1996 |
| EP | 0796653 A2 | 9/1997 |
| EP | 1005901 A2 | 6/2000 |
| EP | 1016452 A2 | 7/2000 |
| EP | 1020167 A2 | 7/2000 |
| EP | 1886647 A1 | 2/2008 |
| EP | 1886648 A1 | 2/2008 |
| EP | 2596873 B1 | 5/2017 |
| JP | 2013-136050 | 7/2013 |
| JP | 2017-185235 | 10/2017 |
| WO | 94/26403 A1 | 11/1994 |
| WO | 95/01809 | 1/1995 |
| WO | 97/18031 | 5/1997 |
| WO | 99/67015 A1 | 12/1999 |
| WO | 00/35506 A1 | 6/2000 |

OTHER PUBLICATIONS

Charnley, J.: Anchorage of the femoral head prosthesis of the shaft of the femur. J. Bone Joint Surg. 42 (1960) 28-30.

* cited by examiner

POWDER-LIQUID BONE CEMENT MIXER WITH COMPRESSED GAS CONNECTION

PRIORITY

This application claims priority under 35 U.S.C. § 119(a) to DE 10 2017 125 592.3, filed on Nov. 2, 2017, the entirety of which is incorporated herein by reference.

TECHNICAL FIELD

The invention relates to a device for producing a bone cement paste from a monomer liquid and a cement powder as parent components of the bone cement paste.

The invention also relates to a method for producing a bone cement paste, in particular a polymethyl methacrylate (PMMA) bone cement paste.

The subject of the invention is in particular a device for the separate storage of the cement powder and the monomer liquid of the PMMA bone cement for subsequent mixing of the cement powder with the monomer liquid to form a bone cement paste and for applying the mixed bone cement paste. The device is determined in particular for the filling of syringes with PMMA bone cement paste for vertebroplasty. Further, the filling of kyphoplasty systems with PMMA bone cement paste is possible. The device according to the invention is preferably a full-prepacked cementing system.

BACKGROUND

PMMA bone cements are based on the fundamental work by Sir Charnley (Charnley, J.: Anchorage of the femoral head prosthesis of the shaft of the femur. J. Bone Joint Surg. 42 (1960) 28-30). The monomer component generally contains the monomer methyl methacrylate and an activator (N,N dimethyl-p-toluidine) dissolved in it. The powder component, also known as cement powder or bone cement powder, has one or more polymers which are produced on the basis of methyl methacrylate and comonomers, such as styrene, methyl acrylate or similar monomers, through polymerization, preferably suspension polymerization, radiopaques and the initiator dibenzoyl peroxide. Upon mixing the powder component, with the monomer component, an elastically deformable paste, the actual bone cement or bone cement paste, is created through swelling of the polymers of the powder component in the methyl methacrylate. During the mixing the powder component with the monomer component, the activator N,N dimethyl-p-toluidine reacts with dibenzoyl peroxide to form radicals. The formed radicals initiate the radical polymerization of the methyl methacrylate. With increasing polymerization of the methyl methacrylate, the viscosity of the bone cement paste increases until it solidifies.

PMMA bone cements can be mixed in suitable mixing bowls with the aid of spatulation through manual mixing of the cement powder with the monomer liquid.

In order to avoid air pockets in the bone cement paste, a plurality of vacuum cementing systems have been described, of which the following are identified here for examplary purposes: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, EP 1 8866 17 A1, and U.S. Pat. No. 5,344,232 A.

Furthermore, devices for mixing PMMA bone cements from two pasty parent components are described in patents DE 10 2010 019 220 B4, EP 2 596 873 B1 and DE 10 2013 226 118 B3, as well as patent application DE 10 2014 101 305 A1.

A further development in cementing technology is a cementing system in which both the cement powder and the monomer liquid are already packed in separate compartments of the mixing devices, and are only mixed together directly prior to the cement application in the cementing system. Such closed full-prepacked mixing devices have been proposed in EP 0 692 229 A1, DE 10 2009 031 178 B3, U.S. Pat. Nos. 5,997,544 A, 6,709,149 B1, DE 698 12 726 T2, EP 0 796 653 A2 and U.S. Pat. No. 5,588,745 A.

The patent DE 10 2009 031 178 B3 discloses a storage and mixing device as a full-prepacked cementing system, in which the parent components required for producing the bone cement paste are initially stored in the storage and mixing device and can be combined and mixed in the storage and mixing device. The storage and mixing device has a two-part delivery plunger for closing a cement cartridge. Here, a combination of a gas-permeable sterilization plunger and a gas-impermeable sealing plunger is used.

After mixing the cement powder with the liquid monomer component, PMMA bone cements are applied in a not yet hardened, paste-like state as bone cement paste. When mixing devices are used, the bone cement paste is located in a cartridge in the case of powder-liquid cements. When applying such conventional PMMA bone cements, after mixing of the two parent components, the bone cement paste formed is pressed out with the aid of a manually operable pressing device. The bone cement paste is pressed out from the cartridge by a movement of a delivery plunger.

When using all full-prepacked cementing systems known to date, the medical user must conduct several working steps in a pre-specified sequence on the devices in series until the mixed bone cement paste is produced and can be applied. If the work steps are conducted in the wrong order, the mixing device may fail and faults in the operation procedure may occur as a result. High-cost training measures by the medical users are therefore necessary in order to avoid user errors.

WO 00/35506 A1 proposes a device in which PMMA cement powder is stored in a cartridge, wherein the cement powder fills the entire volume of the cartridge and the interspaces between the particles of the cement powder have a volume which corresponds to the volume of monomer liquid necessary to produce bone cement paste with the cement powder stored in the cartridge. This device is constructed such that, through the action of a vacuum, the monomer liquid is introduced from above into the cartridge, wherein a vacuum is applied to a vacuum port at the bottom of the cartridge. In this way, the monomer liquid is drawn through the cement powder, wherein the air located in the interspaces between the cement powder particles is displaced by the monomer liquid. This involves no mechanical mixing of the cement dough.

One disadvantage of this system is that cement powders which swell rapidly with the monomer liquid cannot be mixed using this device, because the rapidly swelling cement powder particles form a gel-like barrier once the monomer liquid has penetrated by roughly 1 to 2 cm into the cement powder and prevent migration of the monomer liquid throughout the cement powder. Conventional cement powders additionally suffer from the phenomenon that, due to different surface energies, the cement powder particles are only poorly wetted by methyl methacrylate. The methyl methacrylate thereby penetrates only relatively slowly into the cement powder. Furthermore, the risk cannot be ruled out of the monomer liquid being sucked off via the vacuum port under the action of the vacuum once the cement powder has penetrated fully through the monomer liquid. Then insufficient monomer liquid is available for curing by free-radical polymerization or the mixing ratio is modified undesirably and thus also the consistency of the bone cement paste. It is moreover a problem that the air enclosed between the cement powder particles has to be displaced from the top downwards through the monomer liquid, because the air, which is of a lower specific weight than the monomer liquid, has the tendency, due to gravity, to migrate upwards in the cement powder and not to migrate downwards in the direction of the vacuum port.

Electrically driven expulsion devices are also known from the field of adhesives and sealants. These devices may be driven both with primary and secondary cells and also by a stationary power supply. With their sometimes very significant expulsion forces, these devices may expel particularly viscous, pasty compositions. One disadvantage of the use of electric motors, however, is that they contain non-ferrous metals and are costly to purchase. In the operating area, which must be kept sterile, such devices have to undergo complex sterilization or even be replaced. Electrical wiring may also impede movement of the user while operating.

Pneumatic devices have also been proposed. These apparatuses require a stationary or mobile compressed air connection (e.g., U.S. Pat. No. 2,446,501 A, DE 20 2005 010 206 U1). This necessitates compressed air hoses, which may impede the user's movement.

As an alternative, the use of compressed gas cartridges for providing compressed gas is possible, for pressing out a ready-made adhesive or sealing agent. For this purpose, devices have been recommended in which the inflow of compressed gas is controlled by a valve, and the flow of the viscous mass is additionally controlled by a second valve (e.g., US 2004/0074927 A1, U.S. Pat. No. 6,935,541 B1). With these devices, the gas cartridges are integrated into the devices. With such systems that are connected to compressed air or which contain compressed gas cartridges, a compressed gas source is always required without which the systems are no longer usable.

A series of special PMMA bone cements has been developed for the treatment of impression fractures of vertebrae. These are characterized by the fact that they contain a relatively high proportion of radiopaque, such as zirconium dioxide or barium sulphate. As a result, ongoing monitoring of the spread of the bone cement paste in the fractured vertebra through fluoroscopy is intended to be made easier. The methods currently most commonly used for augmenting fractured vertebrae are vertebroplasty and kyphoplasty. To date, manual mixing of the cement components in mixing bowls or in simple mixing systems is standard. The cement paste formed is then filled into syringes and used as part of the vertebroplasty procedure to augment fractured vertebrae. Alternatively, the cement paste can also be used in kyphoplasty systems, With these systems, a cavity is filled out in the fractured vertebra whereby the vertebra has previously been raised by a balloon. With a plurality of kyphoplasty systems, the cement past is applied using hydraulic systems. This means that the user (the operator) manually operates a hydraulic system via a handpiece, which hydraulically moves a plunger or a membrane, which presses the cement paste through a trocar into the vertebra. Due to the presence of a hose, the handpiece is located approx. 60 cm to 80 cm away from the plunger or the membrane. The advantage of these systems is that the hands of the operator are outside the area of the X-rays due to the hydraulic system.

SUMMARY

The object of the present invention is to overcome the disadvantages of the prior art. In particular, the object of the invention is to develop a device and a method for fixing the parent components of PMMA bone cement, in which the bone cement paste is quickly mixed from a cement powder and a monomer liquid with the least possible effort. The device should here enable a production method, or the method should here be designed such that it runs automatically and independently as far as possible. Electrically driven components should here be used as rarely as possible. The handling of the device should be highly simple compared to cementing systems currently available on the market.

The object of the invention is in particular to develop a device for mixing cement powder and monomer liquid, and preferably also for the prior storage of these parent components, whereby the PMMA bone cement paste formed by mixing of the cement components is preferably determined for the augmentation of fractured vertebrae. The handling of the device should be simplified to the maximum degree in order to generally avoid application errors arising from incorrectly conducted assembly steps. The device should preferably enable safe storage of cement powder and monomer liquid in compartments that are separate from each other, so that during storage of the device, the possibility of unintended mixing of the cement components is excluded. The device should enable sterilization with ethylene oxide gas. The cement powder stored in the device must be accessible to ethylene oxide. The monomer liquid should be mixed without a mixer that must be manually moved from the outside. Following a manual activation, the device should preferably also enable the opening of the monomer liquid container, and independently be able to conduct the subsequent monomer transfer into the cement powder and the mixing of the cement components to form the bone cement paste using an internal energy source. Further, it is important that a suitable connector or a connector with a hose can be applied on the device, via which the bone cement paste formed can be applied into a syringe for vertebroplasty or into a cartridge of a kyphoplasty system.

The invention should also provide a method for producing a bone cement paste, in particular a paste-like PMMA bone cement paste, whereby the bone cement paste is produced from a cement powder and a monomer liquid, with which the disadvantages of the devices and methods to date are overcome. The invention thus also has the object of preventing the formation of monomer bubbles in the bone cement paste produced. With the device according to the invention and the method according to the invention, it should further be achieved that also with a highly simple and low-cost construction of the device, and at the same time highly simple and uncomplicated applicability of the device, a homogeneous bone cement paste can be produced and filled from beginning to end of the pressing procedure.

The construction of the device should be low-cost so that the device can only be used once for hygiene reasons. At the same time, following application, it should be possible to easily dispose of the device without risk. As many processes as possible, or all processes completed in the device, such as mixing of the parent components, the delivery of the bone cement paste and if necessary also the opening of the monomer liquid container and if necessary also the opening of the cartridge, should be completed with the fewest possible work steps and automated as far as possible, and preferably be able to be driven with a single drive.

The objects of the invention are attained by providing a device for producing a bone cement paste from a monomer liquid and a cement powder as parent components of the bone cement paste, the device comprises a cartridge with a cylindrical interior chamber for mixing the parent components, whereby the interior chamber of the cartridge is closed on the front side up to a delivery opening for expelling the bone cement paste from the interior chamber, a deliver plunger which is arranged in the interior chamber of the cartridge and which is supported in a linearly movable manner in the direction of the delivery opening, the cement powder, which is arranged in the interior chamber of the cartridge between the delivery opening and the delivery plunger, a monomer receptacle with an interior chamber in which a monomer liquid container containing the monomer liquid is contained, whereby in the monomer receptacle, a conveying plunger is arranged in the longitudinal direction of the monomer receptacle, a compressed gas connection which is directly connected or connected via a compressed gas line pressure-tight manner with the interior chamber of the monomer receptacle, whereby the conveying plunger is arranged between the monomer liquid container and the compressed gas connection or the compressed gas line in the monomer receptacle, and a connection which connects the interior chamber of the monomer receptacle and the interior chamber of the cartridge which is permeable for the monomer liquid but impermeable for the cement powder, whereby the monomer liquid container is arranged between the conveying plunger and the connection.

According to the invention, the device is preferably also suitable for storing the cement powder and the monomer liquid. For this purpose, it can be provided in a preferred manner that the monomer liquid container is a glass ampule, a plastic ampule, a plastic film bag or an aluminum plastic compound bag. In such monomer liquid containers, the monomer liquid can be stored for a particularly long period of time. Preferably, the monomer liquid container is a glass ampule or a plastic ampule, since these can be reliably punctured by the movement of the conveying plunger and are not susceptible to potential damage.

The interior chamber of the monomer receptacle and the interior chamber of the cartridge may also be connected in a manner permeable for gasses via the connection.

The directions named within the scope of the present invention relate to the direction of flow of the compressed gas, the monomer liquid and the bone cement paste, or to the delivery opening of the device, whereby the delivery opening is arranged at the front on the device or is thus defined at the front. The delivery plunger is therefore driven from behind and moves forwards in the direction of the delivery opening, and at the same time, the bone cement paste is pushed out or pressed out in the direction of the front side through the delivery opening.

The interior chamber of the cartridge has a cylindrical geometry. The cylindrical form is the simplest with which the interior chamber of the cartridge can be realized. Geometrically, a cylindrical form is intended to mean the form of a general cylinder with any base area required, in other words not a cylinder with a circular base area. The interior wall of the interior chamber of the cartridge can therefore be realized by the cylinder sheath, in particular with a different base area. In other words also with non-circular or non-round based areas. According to the invention, however, a cylindrical geometry with a rotation symmetrical and in particular circular base area is preferred for the interior chamber, since this is easiest to produce.

The cartridge, the monomer receptacle, the delivery plunger, the conveying plunger and the connection are preferably produced from a thermoplastic synthetic material, in particular with an injection moulding method.

It can be provided according to the invention that the conveying plunger is pressable with a gas pressure that is guided via the compressed gas connection into the interior chamber of the monomer receptacle in the direction of the connection, and the monomer liquid container is opened by the movement of the conveying plunger, in particular is adapted to be broken open, and the monomer liquid from the interior chamber of the monomer receptacle is adapted to be pressed through the connection into the interior chamber of the cartridge.

As a result, the gas pressure can be used as a drive or as an energy source for opening the monomer liquid container and for pressing out the monomer liquid into the cement powder.

Further, it can be provided that the conveying plunger is impermeable for gases and is sealed in a gas-tight manner against the interior walls of the monomer receptacle, preferably with at least one circumferential seal.

This ensures that the gas pressure can be used for driving the conveying plunger and that no compressed gas is pressed into the monomer liquid.

In one embodiment, the connection has at least one passage in the delivery plunger, whereby the at least one passage is permeable for the monomer liquid and for gasses, and is impermeable for the cement powder, whereby preferably the surface of the delivery plunger that is aligned for the cement powder is adapted to be impermeable to the cement powder.

For this purpose, according to the invention, a porous disc made of plastic can preferably be used.

As a result, the at least one passage can be used for introducing the monomer liquid at the same time, the cement powder cannot penetrate into or through the passage, react there with the monomer liquid, and as a result block the passage or the connection in an unwanted manner, when the cement powder reacts in the connection with the monomer liquid and swells up.

Thus, it is possible for the monomer liquid container containing the monomer liquid to be arranged between the conveying plunger and the delivery plunger.

As a result, it is possible for the monomer liquid container to be pressed together between the conveying plunger and the delivery plunger and as a result opened and pressed out. Here, the delivery plunger is initially held in the cartridge by the cement powder, which is in a non-moistened slate, i.e., when it is not moistened with the monomer liquid, is not flowable and therefore initially holds the delivery plunger in position.

Further, it can be provided that the compressed gas connection has a sealing means for the pressure-tight connection of a compressed gas source, in particular for the pressure-tight connection of a compressed gas cartridge.

In this way, it can be ensured that the compressed gas from the compressed gas source is fully available for the drive of the conveying plunger and does not escape.

in a preferred manner, it can also be provided that the device has a compressed gas cartridge which is connected or is connectable in a pressure-tight manner to the compressed gas connection, whereby preferably the compressed gas cartridge is a $CO_2$ cartridge.

It is hereby achieved that the device is directly usable without further components and without an external compressed gas network.

The recommendation is also made with the invention that the compressed gas connection has a hollow pin for piercing through a membrane of a compressed gas cartridge, the membrane serves as a closure for the compressed gas cartridge.

With this, the compressed gas cartridge can easily be opened within the device.

According to the invention, it can also be provided that the compressed gas connection has inner thread into which a compressed gas cartridge or another compressed gas source with an outer thread can be screwed in.

In one embodiment, it can be provided that the compressed gas connection comprises a valve or an opening device, whereby the opening device is suitable for opening a closed compressed gas cartridge and for producing a pressure-tight connection between the compressed gas connection and the compressed gas cartridge, whereby preferably the compressed gas cartridge and the opening device are supported in the device such that they are movable against each other and the compressed gas cartridge is to be opened in the device through the pushing together of the compressed gas cartridge and the opening device, so that compressed gas flows from the compressed gas cartridge into the interior chamber of the monomer receptacle.

As a result, the device can be conveniently activated by operating the valve or the opening device, so that it then mixes the bone cement paste.

Further, it can be provided that the device has a container for a compressed gas cartridge, whereby a compressed gas cartridge inserted into the container is to be opened in the device by a movement of the compressed gas cartridge against the compressed gas connection such that the compressed gas flows out of the compressed gas cartridge into the compressed gas connection, whereby preferably the compressed gas cartridge is to be moved by a screw movement against the compressed gas connection.

Preferably, the screw movement can be generated by manual operation of an actuation element, in particular by manual turning of a wing screw head.

Through these measures, the device can be conveniently activated by moving the container for the compressed gas cartridge or compressed gas source so that it then mixes the bone cement paste. The device is fully ready for use with the inserted compressed gas cartridge or compressed gas source.

It can be provided according to the invention that in the compressed gas connection or in the compressed gas line, a discharge valve is arranged for discharging an overpressure into the environment, in particular a closed discharge valve that is manually operable from the outside or a closed discharge valve that is mechanically or electrically openable.

As a result, the device can be made pressure-free after the production of the bone cement past and thus disposed of without risk after use.

It can also be provided that the connection has a fluid line, whereby the fluid line connects the interior chamber of the monomer receptacle with the interior chamber of the cartridge.

As a result, the cartridge and the monomer receptacle can be arranged parallel to each other or adjacent to each other, and thus the device can be designed in a compact manner.

It can be provided according to the invention that between the connection and the monomer liquid container, an elasticity deformable spacer is arranged, whereby preferably, the space separates the monomer liquid container from the connection by at least 3 mm, preferred at a distance of at least 6 mm from the connection, or preferred at a distance of at least 10 mm from the connection.

With the spacer, the monomer liquid container can be stored in the monomer receptacle in a shockproof manner.

Further, it can be provided that the connection opens out into the interior chamber of the cartridge via a confluence in a side wall of the cartridge, whereby the confluence is covered by a side area of the delivery plunger which lies parallel to the direction of movement of the delivery plunger, whereby the delivery plunger has a passage into the interior chamber of the cartridge to the cement powder which is permeable for the monomer liquid, which extends from a side area of the delivery plunger up to a front base area of the delivery plunger, whereby the base area of the delivery plunger lies vertical to the direction of the movement of the delivery plunger, whereby preferably the passage is impermeable for the cement powder and preferably is permeable for gases.

As a result, the cartridge and the monomer receptacle can be arranged parallel to each other or adjacent to each other, and thus the device can be designed in a compact manner. Additionally, in this manner, the opening into the interior chamber of the cartridge is closed by the driving forward of the delivery plunger, so that no further monomer liquid can flow into the interior chamber of the cartridge and thus, an even consistency of the bone cement paste can be better guaranteed.

With such a design, it can be provided according to the invention that the delivery plunger is forward-drivable towards the delivery opening via a drive rod or a threaded rod in the cartridge.

In this manner, the bone cement paste can be conveniently filled from the cartridge into an applicator such as syringe, or directly applied.

It can also be provided that on the delivery opening, a tube or hose is connected, whereby preferably, a Luer lock adapter is provided at the tip of the application tube or the hose.

As a result, the device can also be used to apply the bone cement paste through a hose system or a trocar.

Additionally, it can be provided that an additive conducting the monomer liquid is distributed in the cement powder, whereby preferably the cement powder is coated with the additive or mixed with the additive in the cement powder.

As an additive, a biocompatible cellulose can be used, for example, which has sufficient suction capacity for the monomer liquid. The additive can be distributed in particles in the cement powder.

It can hereby be achieved that the monomer liquid is quickly distributed in the cement powder, and thus full mixing occurs before the swelling of the cement powder prevents a further dissemination of the monomer liquid. As a result, it is possible to also guide the monomer liquid over longer distances through the cement powder and, thus, produce a homogenous bone cement paste.

Further, it can be provided that in the cartridge, a monomer liquid is contained as a first parent component and a powder is contained as a second parent component, from which the bone cement past is mixed within the cartridge, whereby in the powder, a hydrophilic additive is distributed with which the monomer liquid is distributable in the entire powder, preferably without polymerization of the bone cement paste previously preventing the further distribution of the monomer liquid in the powder.

It is hereby achieved that the monomer liquid is quickly distributed in the powder, before polymerization of the cement powder contained in the powder occurs with the monomer liquid, and as a result, further distribution of the monomer liquid is prevented. Only as a result of this is the construction according to the invention in a single cartridge possible at all, that namely the monomer liquid is pressed from one side into the powder and yet can be distributed in the entire powder before polymerization prevents further distribution of the monomer liquid in the powder.

The additive is preferably particulate or fibrous. Preferably, the additive has a chemical substance with at least one OH group. The additive preferably has a suction capacity of at least 0.6 g of methyl methacrylate per gram of additive.

It can be provided according to the invention that the powder has at least one particulate PMMA or PMMA copolymer with a sieve fraction of less than 100 μm, an initiator and at least one additive that is indissoluble in methyl methacrylate, particulate or fibrous, whereby the additive has a suction capacity larger than or equal to 0.6 g of methyl methacrylate pre gramme of additive at room temperature.

Such a powder is particularly suited for the distribution of the monomer liquid, so that a construction of the bone cement applicator is enabled with which a single-sided pressing in of the monomer liquid is also possible on a narrow side of the interior chamber of the cartridge. Here, it was surprisingly found that it is possible, through simply bringing into contact of such a powder and in particular of a powder defined below with a monomer liquid, in particular with a monomer liquid defined below, to produce adhesive-free, elastically formable bone cement paste which hardens independently through radical polymerization without it being necessary to manually mix the cement paste or to mix it with the aid of technical auxiliary means. It was observed that by adding an additive that is indissoluble in methyl methacrylate, particulate or fibrous, which has suction capacity of greater than 0.6 g of methyl methacrylate per gramme of additive at room temperature, to a cement powder of a low-viscosity bone cement, a modified powder is obtained as cement powder, into which the monomer liquid can be pressed in over a distance of at least 5 cm. Surprisingly, the additive also improves the moisturization of the cement powder with monomer liquid. The additive here has a "wick effect" and even with very small quantities of 0.1 weight % and above guides the monomer liquid into the interior of the powder. Further, the additive delays the adhesion of the polymer particles in the powder, as a result of which the formation of a blocking gel layer is delayed and the penetration of the monomer liquid into the powder is facilitated. Here, the monomer liquid can be pressed in or also sucked into the powder.

Here, it can preferably be provided that the additive has covalently bonded hydroxyl groups on its surface. According to the invention, the additive can preferably be selected from the group consisting of microcrystalline cellulose, oxycellulose, starch, titanium dioxide and silicone dioxide, whereby pyrogenic silicone dioxide is particularly preferred. The additive can have a particle size with a sieve fraction of less than 100 μm, preferably a sieve fraction less than 50 μm, and more preferred, a sieve fraction less than 10 μm. Further, it can preferably be provided that the additive is contained in the powder in a quantity of 0.1 to 2.5 weight % in relation to the overall weight of the powder. Furthermore, it can be provided that the polymer powder contains dibenzoyl peroxide as an initiator.

It can be provided that the monomer liquid contains at least one methyl methacrylate and one activator. Furthermore, it can be provided that the monomer liquid contains at least one activator from the group of aromatic amines. Further, it can be provided that the monomer liquid contains at least one radical stabilizer from the group of quinones or sterically hindered phenols.

Here, it is advantageous when the additive has covalently bonded hydroxyl groups on its surface. Here, Si—OH groups and alcoholic OH groups are particularly advantageous. Due to the OH groups arranged on the surface, the additive has a high surface energy, as a result of which good moisturizing capacity of the additive with methyl methacrylate is achieved. The pyrogenic silicic acids Aerosil® 380 and Aerosill® 300 are particularly suitable. Additionally, it is also possible to use the silicone dioxide produced through sol-gel processes as an additive.

For this purpose, it can also be provided that the interior chamber of the cartridge and the interior chamber of the monomer receptacle form a shared cylindrical interior chamber and align with each other, so that the delivery plunger is forward drivable with the conveying plunger in the interior chamber of the cartridge and the conveying plunger is pressable into the interior chamber of the cartridge.

As a result, the delivery plunger can be driven by driving forward the conveying plunger with the compressed gas. As a result, due to the relaxing compressed gas, not only the bone cement paste can be produced, but it can also be driven out of the cartridge for further use.

According to the invention, it can preferably be provided that on the interior wall of the cartridge in the area of the front side, a bypass or a groove is provided, through which the compressed gas can flow past the conveying plunger and the delivery plunger when the conveying plunger has traversed an opening to the bypass or the groove at least in regions, and as a result has opened it up to the compressed gas connection.

As a result, the compressed gas escapes out of the device through the bypass or the groove at the end of the pressing out procedure and the device is thus rendered pressure-free and can be disposed of without risk.

Here, it can be provided that the opening for the bypass or the end of the groove is at a greater distance from the front end of the cartridge than the total of the height of the conveying plunger and the delivery plunger, preferably at least more than 5 mm and the maximum of 20 mm further away the front end of the cartridge than the total of the height of the conveying plunger and the delivery plunger.

It is hereby ensured that the bone cement paste is fully driven out of the cartridge before the device becomes pressure-free.

Preferably, it can furthermore also be provided that on the compressed gas connection or in the compressed gas line, a sterile filter is arranged which sterilely filters a compressed gas flowing into the monomer receptacle.

A potential dirtying or contamination by the compressed gas used is hereby avoided.

Preferably, it can be provided that on the compressed gas connection or in the compressed gas line, a closed overpressure valve is arranged which when a threshold pressure is exceeded opens up the compressed gas connection or the compressed gas line outwards to the environment.

It can hereby be avoided that the device, in particular the monomer receptacle, explodes.

Further, it can be provided that the device has a closure that closes the delivery opening and which is movably supported against the delivery opening, whereby a line element is arranged on the front side of the delivery opening, whereby the line element comprises a closure holder for holding at least a portion of the closure, and whereby the closure is pressable into the closure holder through a pressure onto the bone cement paste such that the delivery opening is opened, whereby the line element with the closure pressed into the closure holder provides a free line cross-section, through which the bone cement paste is pressable out through the delivery opening and out of the device.

The device is hereby initially closed and opens independently through the driving forward of the bone cement paste with the delivery plunger.

It can be provided that the closure is permeable for gases but impermeable for the cement powder.

As a result, the interior of the cartridge can be sterilised with a sterilising gas such as ethylene oxide.

With devices with a closure, it can be provided that the bone cement paste flows around the closure in the closure holder when the bone cement paste flows through the line element, preferably the bone cement past flows past the closure along at least one side surface or sheath surface of the closure.

The fact that the bone cement paste flows around the closure in the closure holder means that the bone cement paste flows past the closure in the longitudinal direction of the closure.

It is hereby achieved that the construction can be kept very simple, since no additional channels need to be provided through which the bone cement paste flows around the closure in guiding means. Additionally, the bone cement paste is pressed into the direction of movement of the closure, so that the force that is transferred with the bone cement paste and which is used to provide the flow of the bone cement paste does not have to be diverted, as a result of which the force required to open the device and to drive out the bone cement paste can be kept at a low level.

With devices according to the invention with a closure, it can also be provided that the free line cross-section on one side is delimited at least in sections by the closure, preferably by a side surface or a sheath surface of the closure.

It is hereby also achieved that the bone cement paste can be pressed into the direction of movement of the closure, also in order to flow through the line element, so that the force that is transferred with the bone cement paste and which is used to provide the flow of the bone cement paste does not have to be diverted, as a result of which the force required to open the device and to drive out the bone cement paste can be kept at a low level.

Furthermore, it can be provided that the closure is inserted in a fixed manner in the closure holder when it is pressed into the closure holder out of the delivery opening.

It is hereby prevented that the closure moves in the closure holder when it is arranged in the flowing bone cement paste. As a result, a change to the flow resistance of the bone cement paste and a time change of the volume flow of the bone cement paste is prevented.

In order to simplify the construction, it can be provided that the closure is cylindrical at least in sections, in particular is fully cylindrical, and the closure holder forms a hollow cylindrical sleeve, whereby preferably, in the sheath surface of the hollow cylindrical sleeve, at least one channel is provided, whereby the at least one channel provides the free line cross-selection.

This design is easy to produce. Additionally, the closure can be moved in the axial direction of its cylindrical geometry, so that the movement can be conducted in an easy manner.

Here, it can be provided that the inner diameter of the hollow cylindrical sleeve is greater than the outer diameter of the closure, preferably at least 1 mm greater than the outer diameter of the closure, particularly preferred between 1 mm and 10 mm greater than the outer diameter of the closure.

The free line cross-sections that result from this are arranged such or are of such a size that they only slightly impair the flow of the bone cement paste.

According to a preferred further development of the present invention, it can be provided that spacers are provided in the closure holder for distancing the closure from the interior wall of the closure holder, whereby preferably, the spacers are bars that in a particularly preferred manner are aligned in the direction of movement of the closure and/or are aligned in the direction of flow of the bone cement paste.

As a result, it is achieved that the free line cross-section is achieved through the distancing of the closure from the interior wall of the closure holder when the closure is pressed into the closure holder.

Further, it can be provided that the free line cross-section is at least half as large as the profile of the delivery opening preferably at least the same size as the profile of the delivery opening.

As a result, the flow resistance for the bone cement paste is not impaired by a too low free line cross-section of the line element and at the same time, the construction of the device is compact.

Preferably, it can also be provided that in the closure holder on the front wall facing away from the delivery opening, a stop is arranged for limiting the movement of the closure, whereby the stop distances the closure when fully pressed in from the front wall on the front side of the closure holder so that between the front side of the closure and the front wall, the free line cross-section remains.

It is hereby achieved that the bone cement paste can be further guided or can flow behind the line element in the same direction in which it flows while the closure is being pressed into the closure holder.

It can also be provided that the rear side of the cartridge is connected with the front side of the monomer receptacle, preferably connected such that the interior chamber of the cartridge aligns with the interior chamber of the monomer receptacle.

As a result, the conveying plunger can also be used to drive the delivery plunger, and thus the bone cement paste can also be driven out of the cartridge with the conveying plunger driven by the compressed gas. The device is here a full-prepacked cementing system. Due to the aligned interior chambers of the cartridge and the monomer receptacle, it can be ensured that first the conveying plunger can be moved by a gas pressure acting on the rear side the conveying plunger, and then the conveying plunger can be used to drive the delivery plunger, whereby the conveying plunger together with the delivery plunger (and if necessary with the shards of a glass or plastic ampule as a monomer liquid container between them) is further pressed in the direction of the delivery opening.

Preferably, it can be provided that the monomer receptacle has a cylindrical interior chamber. Here, too, the cylindrical form is the simplest with which the interior chamber of the receptacle can be realized. Geometrically, a cylindrical form is intended to mean the form of a general cylinder with any base area required, in other words not a cylinder with a circular base area.

It can be provided that on the front side of the conveying plunger, at least one protruding tip, edge and/or blade for breaking the monomer liquid container is arranged.

Through the use of a defined force on a predetermined, spatially delimited site, the pressure on this site can be increased with the same force, and thus a defined breaking of the monomer liquid container is achieved. As a result, the procedure of breaking open the monomer liquid container is reproducible.

Further, it can be provided that in the compressed gas connection or in the monomer receptacle, a ventilation opening is provided, whereby the ventilation opening is closable through a movement of the compressed gas connection or through a movement of a container for a compressed gas cartridge.

The interior chamber of the monomer receptacle is hereby accessible to a sterilising gas such as ethylene oxide.

Further, it can be provided that on the front side of the delivery plunger facing towards the delivery opening, a hollow cylinder is arranged, whereby the hollow cylinder is open on its front side facing towards the delivery opening and the hollow cylinder preferably extends from the front side of the delivery plunger at least 3 mm into the interior chamber of the cartridge.

With the hollow cylinder on the front side of the delivery plunger, it is not possible to allow to flow or to guide the monomer liquid through the cement powder during pressing into the cement powder in the interior chamber of the cartridge over a longer distance, before the monomer liquid reaches the interior wall of the cartridge. As a result, the formation of monomer liquid bubbles or pockets of the monomer liquid in the bone cement paste formed can be avoided or reduced. Thus, a more homogeneous bone cement paste can be produced. Further, it has been found that through the retention of a small residue of the bone cement paste created in the cartridge as a mixture of the cement powder with the monomer liquid in the interior chamber of the cartridge, it is achieved that at the end of the pressing out procedure, no bone cement paste is delivered with an altered consistency, since the remaining bone cement paste is retained in the cartridge and the delivery opening is closed.

Here, it can be provided that the hollow cylinder blocks a further movement of the delivery plunger in the direction of the front side of the cartridge when the front side of the hollow cylinder lies on the front side of the interior chamber of the cartridge, so that the delivery plunger is at a distance from the front side of the interior chamber of the cartridge and a dead volume remains in the interior chamber of the cartridge.

The hollow cylinder is arranged in the interior chamber of the cartridge. Preferably, the front side of the delivery plunger is even with the exception of the hollow cylinder.

It can preferably be provided that the delivery plunger is tight or sealed against the interior wall of the interior chamber of the cartridge, in particular sealed with at least one circumferential seal.

Further, it can be provided that the hollow cylinder has at least one slit, preferably a slit running parallel to the cylinder axis of the hollow cylinder, particularly preferred at least one slit reaching from the front side to the delivery plunger.

As a result, the fitting of the hollow cylinder to the interior wall of the cartridge can be more easily adjusted and the risk of a blockage of the movement of the delivery plunger with the hollow cylinder is reduced. As an alternative, the at least one slit can also run in the form of a spiral in the walls of the hollow cylinder, as well as parallel to the cylinder axis of the hollow cylinder.

It can also be provided that, in the delivery plunger at least one connection is provided from the rear side of the delivery plunger to the front side of the delivery plunger for introducing the monomer liquid into the interior chamber of the cartridge, whereby the at least one connection is permeable for the monomer liquid and gases and impermeable for the cement powder.

It can be provided that the cement powder rests against the front side of the delivery plunger, in particular over its full surface, whereby preferably, the cement powder is pressed into the interior chamber of the cartridge.

As a result, it is prevented that larger gas pockets remain in the cartridge, which when mixing the monomer liquid with the cement powder could lead to gas pockets in the bone cement paste or to the formation of monomer liquid bubbles. This cannot occur with a densely poured or preferably pressed cement powder, since the monomer liquid moistens the particles of the conveying plunger well and the surface tension of the monomer liquid then permits no or at least no relevant gas pockets between the particles of the cement powder.

It can also be provided that the cement powder fully fills out the interior chamber of the cartridge between the closed front side and the delivery plunger, whereby preferably, the cement powder is pressed into the interior chamber of the cartridge.

It is hereby achieved that the monomer liquid penetrates into the intermediate spaces between the powder particles of the cement powder and can there be guided through the cement powder by capillary forces and thus be well distributed. As a result, a fast, even distribution of the monomer liquid in the cement powder is therefore achieved.

The objects that form the basis for the present invention are also attained by a method for producing a bone cement paste, in particular a paste-like PMMA bone cement paste, whereby the bone cement paste is produced from a cement powder and a monomer liquid, whereby the monomer liquid is contained in a monomer liquid container, which is arranged in a monomer liquid container, and whereby the cement powder is contained in a cartridge, characterized by the following steps that are conducted in succession:

a) Driving and moving a conveying plunger in the monomer receptacle with a compressed gas, whereby with the movement of the conveying plunger the monomer fluid from the monomer fluid container and from the monomer receptacle is pressed into the interior chamber of a cartridge, so that the monomer fluid mixes with the cement powder in the cartridge and there forms the bone cement paste, b) The mixed bone cement paste is pressed out of a delivery opening with a delivery plunger on a side of the cartridge opposite the delivery plunger.

Here, it can be provided that the bone cement paste is produced with a device according to the invention.

Additionally, it can be provided that in the monomer liquid is distributed in the cement powder with the aid of an additive that guides the monomer liquid, whereby particles of the cement powder are coated with the additive or mixed with the additive.

It can hereby be achieved that the monomer liquid is quickly distributed in the cement powder, and thus full mixing occurs, before the swelling up cement powder prevents a further dissemination of the monomer liquid. As a result, it is possible to also guide the monomer liquid over longer distances through the cement powder, and thus produce a homogeneous bone cement paste.

For the same purpose, it can be provided that the cement powder is fully moistened by the monomer liquid, whereby for this purpose, preferably an additive that attracts the monomer liquid is distributed in the cement powder.

It can also be provided that the monomer liquid container is opened by the movement of the delivery plunger driven by the compressed gas.

Hereby, the drive already present from the compressed gas is also used to open the monomer liquid container. As a result, a further automation of the method is achieved.

Further, it can be provided that the mixed bone cement paste is filled from the cartridge into an applicator or a syringe.

In this manner, the bone cement paste can later be conveniently applied with the applicator or the syringe.

It can further be provided that in step b), the delivery plunger is pushed by the conveying plunger driven by the compressed gas in the direction of the delivery opening.

The drive provided by the compressed gas is hereby also used to press out the bone cement paste from the cartridge and thus the method is further automated.

It can also be provided that during pressing in of the monomer liquid into the cartridge, gas is suppressed from the intermediate spaces of powder particles of the cement powder, and pressed out of the delivery opening, in particular by a closure in the delivery opening that is permeable for gas but impermeable for the cement powder.

Thus the penetration of the monomer liquid in the cement paste is facilitated.

It can also be provided that the conveying plunger is pressed into the interior chamber of the cartridge and at the end of its movement opens up an opening to a bypass or a groove in the side interior wall of the cartridge, whereby the compressed gas escapes outwards through the bypass or the groove past the conveying plunger and the delivery plunger, in particular through the delivery opening.

As a result, the compressed gas escapes out of the device through the bypass or the groove at the end of the pressing out procedure and the device is thus rendered pressure-free and can be disposed of without risk.

It can be provided according to the invention that a closure is pressed by the pressure of the bone cement paste acting on the closure into a closure holder and at the same time, the delivery opening is opened, whereby preferably, when pressing out the bone cement paste from the delivery opening, the bone cement paste flows through a free line cross-section created by the opening of the closure and is delivered out of the device.

The cement powder can hereby initially be stored closed and the cartridge is independently opened by the driven bone cement paste.

Further, it can be provided that prior to step a), the compressed gas cartridge is opened and the compressed gas is guided into the conveying plunger from the compressed gas cartridge through a compressed gas connection into the monomer receptacle.

Thus, the method can be applied independently of external compressed gas sources.

It can be provided that on the front side of the delivery plunger facing towards the delivery opening, a hollow cylinder is arranged, whereby the monomer liquid flows around the hollow cylinder before it reaches the interior wall of the cartridge and/or the delivery plunger impacts on the front side of the cartridge, whereby with the hollow cylinder, a further movement of the delivery plunger in the direction of the delivery opening is blocked and a residual quantity of the bone cement paste remains in the portion of the interior chamber of the cartridge that is delimited by the hollow cylinder.

With the application with the hollow cylinder, it is ensured that at the end of the pressing out procedure, a poorly mixed residue of the bone cement paste or a portion of the bone cement paste that has an altered composition is retained in the cartridge and is not used for application.

It is also recommended with the method according to the invention that in step a) the monomer liquid is pressed into the cartridge through at least one connection that is impermeable for the cement powder but permeable for gases and the monomer liquid, preferably pressed into the cartridge through a movement of conveying plunger which is driven with the compressed gas.

It is hereby prevented that the monomer liquid mixes with the cement powder at an early stage.

The invention is based on the surprising finding that with a conveying plunger driven by a compressed gas, it is possible to press a monomer liquid deeply into a cement powder in a cartridge such that the monomer liquid is evenly distributed in the cement powder and thus a homogeneous bone cement paste is formed. At the same time, the movement of the conveying plunger driven with the compressed gas can also be used to open a monomer liquid container in which the monomer liquid is contained. In a preferred embodiment, the movement driven by the compressed gas can in addition be used for driving out the bone cement paste from the cartridge, whereby for this purpose, a delivery plunger is driven by the movement of the conveying plunger.

The particular advantage of the invention is that the user is provided with bone cement paste within a period of a few seconds, without the user having to conduct complex steps to open the monomer liquid container and to mix the parent components, and to press out the cement paste in syringes or in kyphoplasty systems.

The device can be used as a hygienic disposable product, since it can to a very large extent be produced from plastic and since all parts including the interior chambers and the conveying plunger are sterilisable with the aid of the ethylene oxide.

An exemplary device according to the invention for storing, mixing and delivering PMMA bone cement paste can for example have:
a) a hollow cylindrical cartridge,
b) a conveying plunger arranged in the cartridge that is impermeable for gasses and axially movable,
c) a delivery plunger arranged in the cartridge that is impermeable for powder particles and axially movable,
d) a monomer liquid container with a monomer liquid which is arranged in a first hollow chamber, which is delimited by the hollow cylindrical cartridge, the conveying plunger and the delivery plunger,
e) a first cartridge closure that is permeable for gases but impermeable for powder particles, which is arranged such that it is axially movable in the cartridge,
f) cement powder arranged in a second hollow chamber which is delimited by the interior chamber of the cartridge, the delivery plunger and the first cartridge closure,
g) a second cartridge closure that closes the cartridge below the conveying plunger,
h) a third hollow chamber that is delimited by the cartridge, the conveying plunger and the second cartridge closure, i) a gas cartridge with an opening element to be actuated manually, whereby the gas cartridge contains compressed gas, and j) a gas-permeable compressed gas line, which connects the gas cartridge with the third hollow chamber in a gas-permeable manner.

A method according to the invention can for example be implemented with the exemplary device for mixing the conveying plunger with the monomer liquid to form bone cement paste with the following successive steps:

a) manually actuating of the opening element of the gas cartridge, b) opening of the gas cartridge, c) flowing out of the compressed gas from the gas cartridge through the compressed gas line into the third hollow chamber, d) pushing of the conveying plunger in the direction of a delivery opening in a front cartridge head, e) bursting of the monomer liquid container by the movement of the conveying plunger, f) pressing out of the monomer liquid from the first hollow chamber and through the delivery plunger into the cement powder in the second hollow chamber, g) suppression of the air from the intermediate spaces of the conveying plunger particles, h) escaping of the suppressed air through the first cartridge closure, i) full moistening of the conveying plunger particles while at the same time forming the bone cement paste, j) pushing the conveying plunger onto the burst monomer liquid container and the delivery plunger, k) pressing the bone cement paste in the direction of the first cartridge closure, l) moving out or opening the first cartridge closure from the cartridge, and m) flowing out of the bone cement paste from the cartridge head.

BRIEF DESCRIPTION OF THE DRAWINGS

Below, further exemplary embodiments of the invention will be explained with reference to fifteen drawings, without thereby limiting the invention. In the drawings.

DETAILED DESCRIPTION

For purposes of simplification, the same reference numbers are used for some identical components in the figures even if the embodiments are different.

Figure 1A:
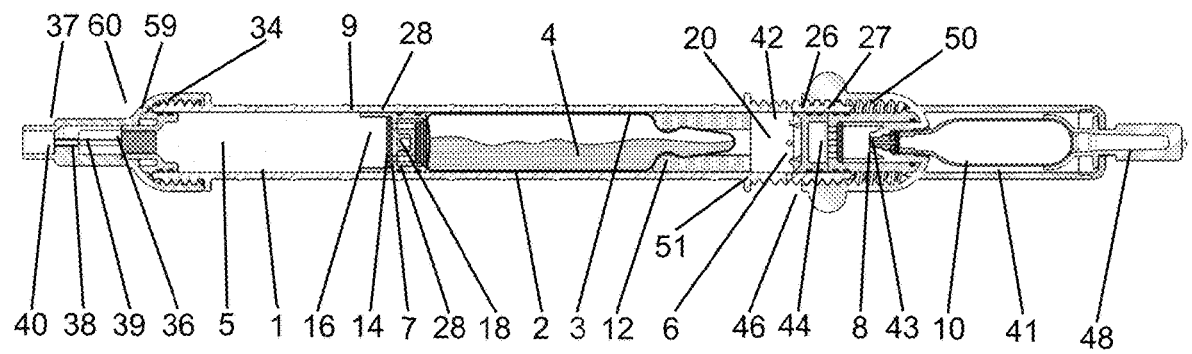
FIGS. 1A to 1E: show five schematic profile views of a first device according to the invention for storing and mixing a monomer liquid and a conveying plunger over each other to clearly illustrate the procedure of a method according to the invention.
Figure 1B:
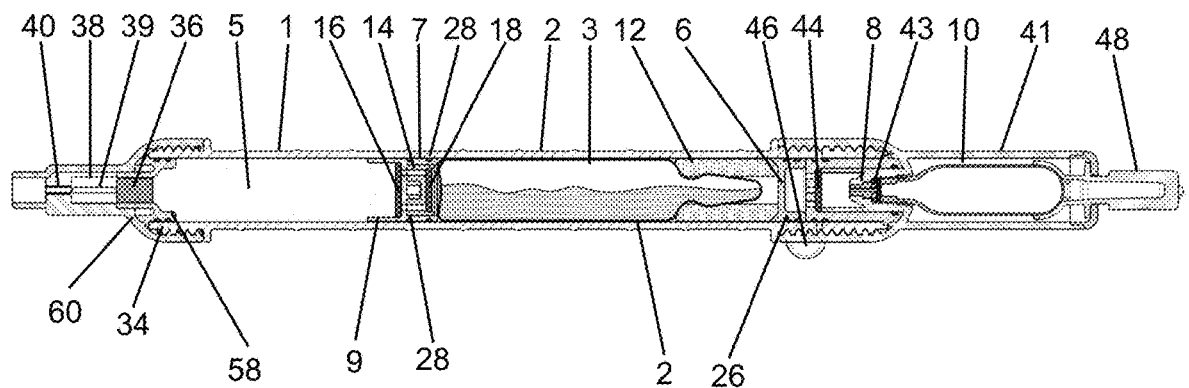
Figure 1C:
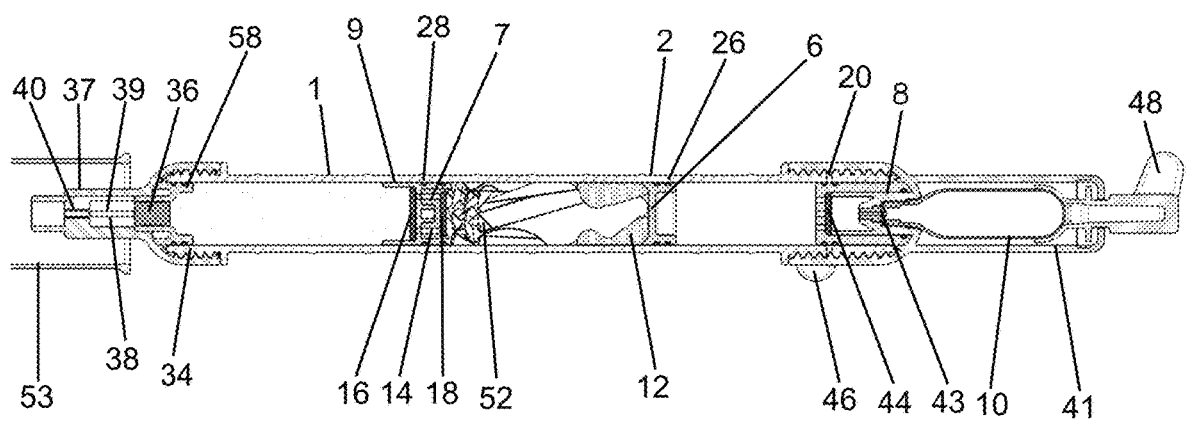
Figure 1D:
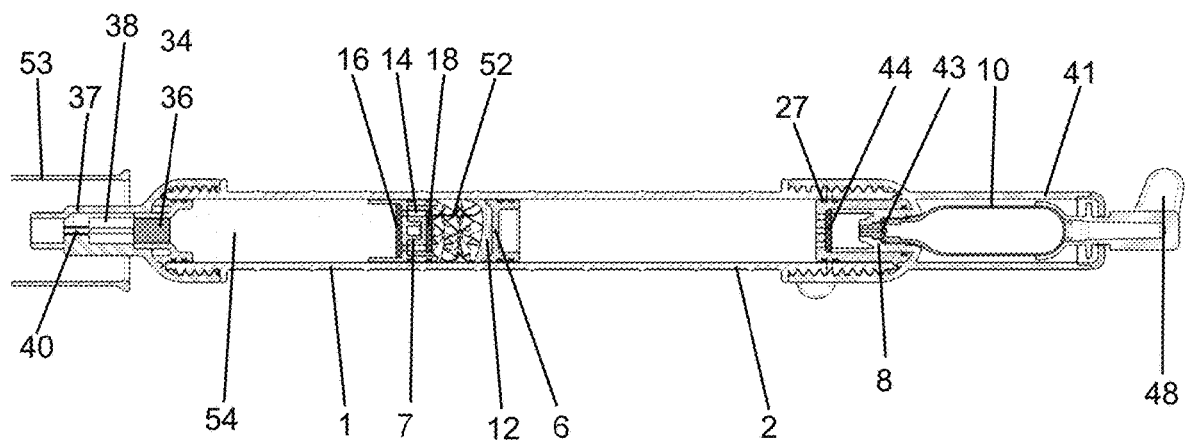
Figure 1E:
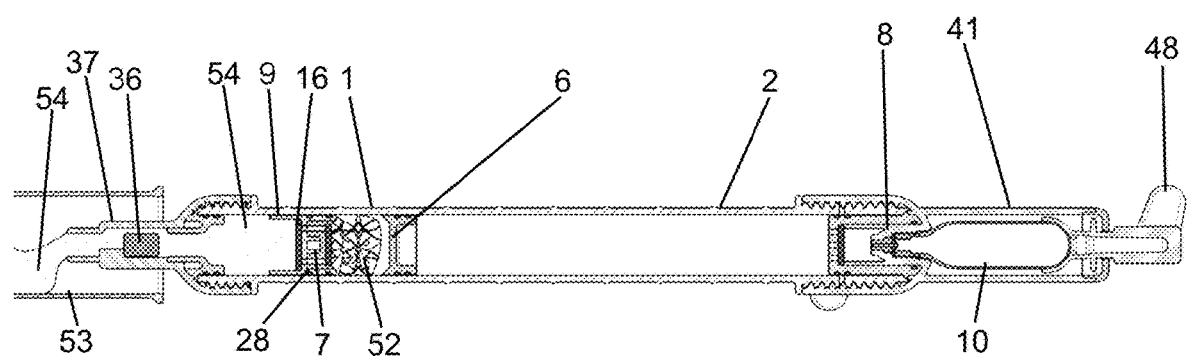
Figure 2:
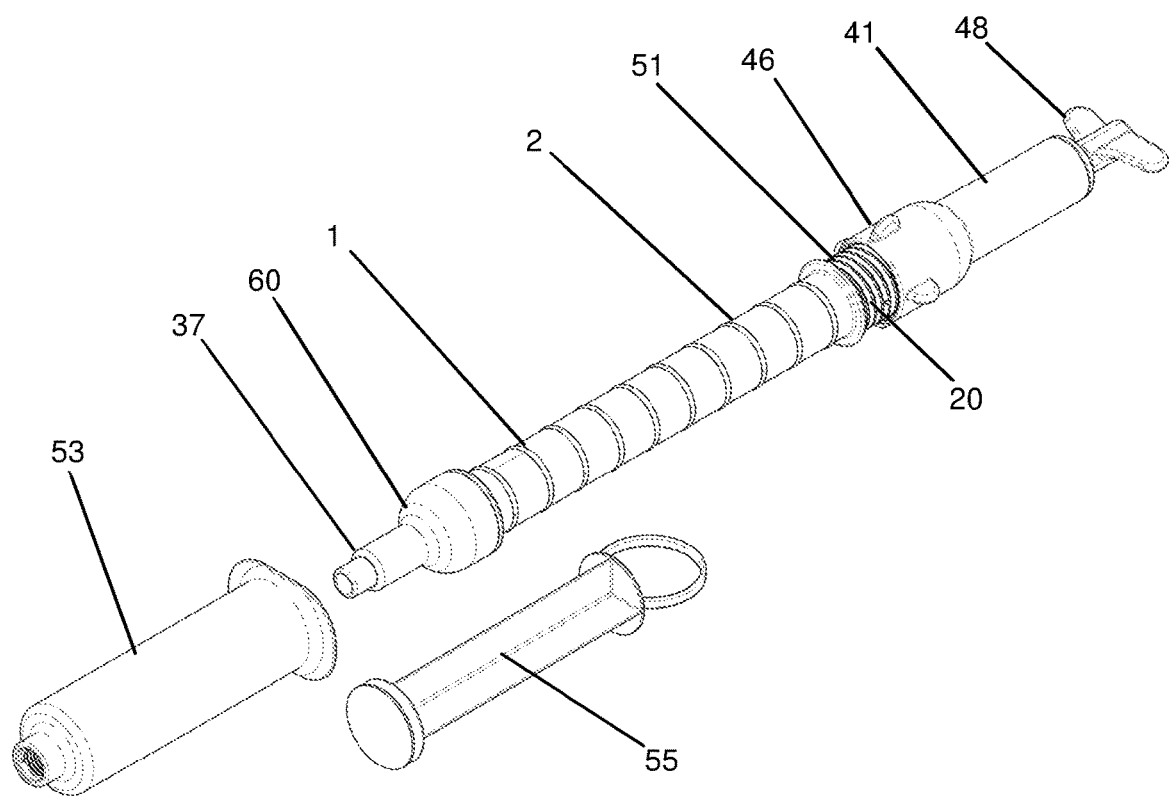
FIG. 2: shows a schematic perspective external view of the first device according to FIGS. 1A to 1E with a syringe for applying the bone cement paste.
Figure 3A:
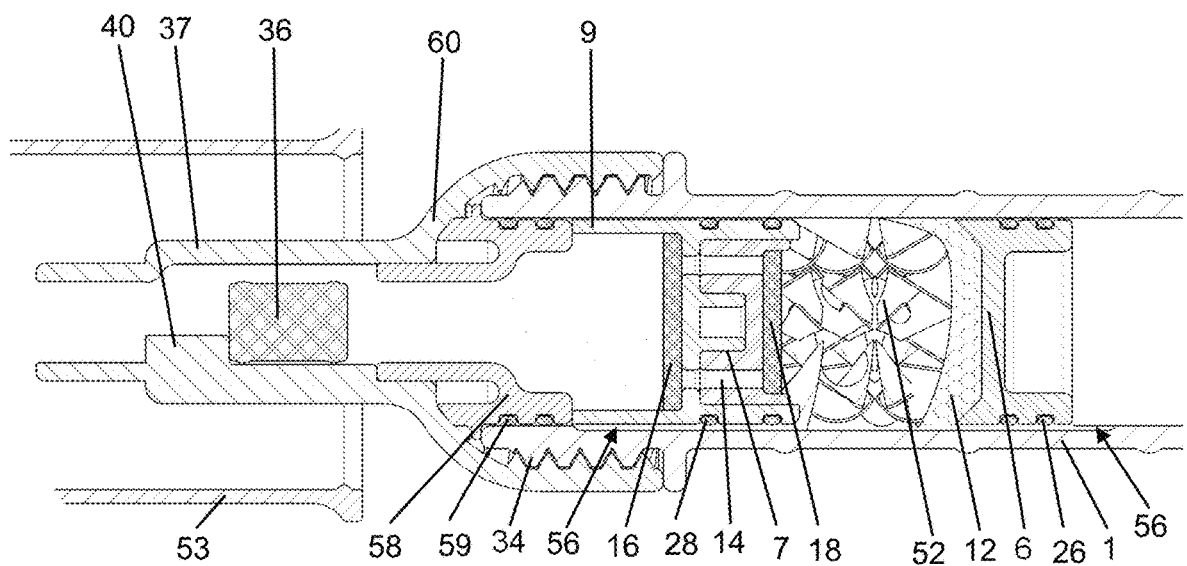
FIGS. 3A and 3B: show two schematic profile views as section enlargements of the first device according to FIGS. 1A to 1E and 2 over each other during pressing out of the bone cement paste, whereby the profile planes are vertical to each other.
Figure 3B:
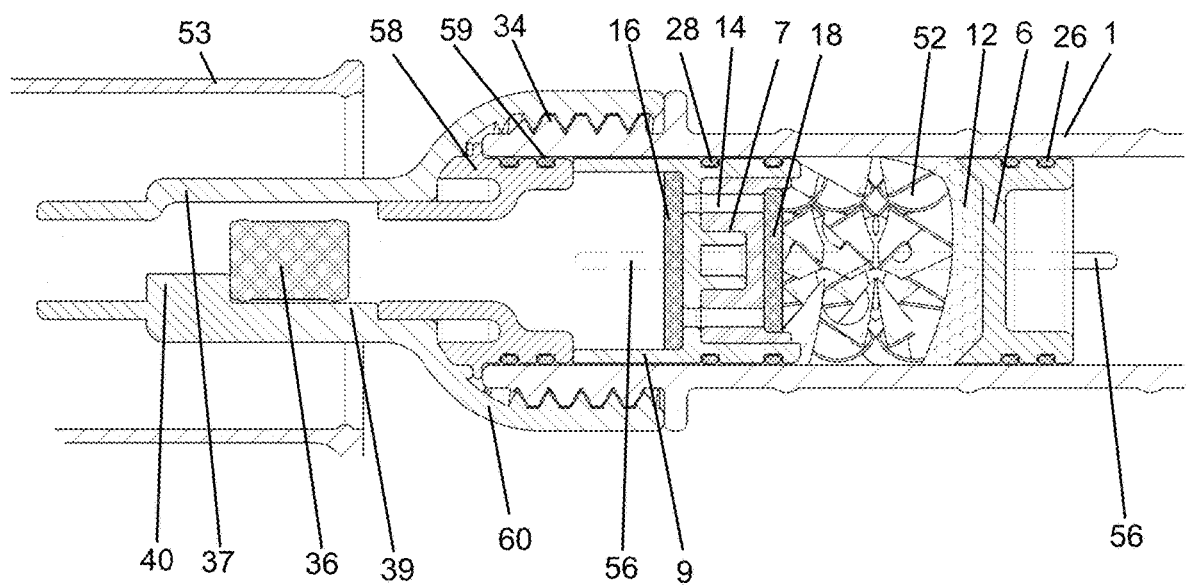

In FIGS. 1A to 1E, 2, and 3A to 3B, illustrations of a first device according to the invention for storing and mixing a monomer liquid and a conveying plunger in order to produce a bone cement paste are shown. FIGS. 1A to 1E show five profile views over each other to explain the procedure of a method according to the invention, whereby the state of the device changes from FIG. 1A to 1E during the method. FIG. 2 shows a perspective external view and FIGS. 3A and 3B show two profile views as section enlargements with profile planes arranged vertically to each other.

The first device according to the invention comprises, consists essentially of, or consists of, a tubular container made of plastic, which as a front portion (on the left in FIGS. 1A to 1E and 2) forms a cartridge 1 with a cylindrical interior chamber and which as a rear portion forms a monomer receptacle 2 for a glass ampoule 3 as a monomer liquid container. Instead of the glass ampoule 3, a plastic ampoule that can be broken open can easily be used, or with slight conversion measures, a tear-openable film bag that made of a metal-coated plastic can be used instead of the glass ampoule 3.

The rear side of the device is shown on the right in FIGS. 1A to 1E and 2. The tubular form of the container can easily be detected in the profile views of FIGS. 1A to 1E and the perspective view according to FIG. 2. Both the interior chamber of the cartridge 1 and the interior chamber of the monomer receptacle 2 are cylindrical with a circular base area. Here, the diameter of the interior chamber of the cartridge 1 and the diameter of the interior chamber of the monomer receptacle 2 are equally large and align. The container with the monomer receptacle 2 and the cartridge 1 is preferably made of plastic using the injection moulding technique. The monomer receptacle 2 thus has a cylindrical interior chamber into which the glass ampoule 3 is inserted. The monomer liquid 4 is located in the glass ampoule 3. In the interior chamber of the cartridge 1, a cement powder 5 is filled in or preferably pressed in. The monomer liquid 4 and the cement powder 5 form the parent components for a PMMA bone cement that is producible with the device. Due to the glass ampoule 3, the monomer liquid 4 can be stored for a very long period of time in the monomer receptacle 2 and as a result in the device. The cement powder 5 can also be stored for longer periods of time in the device. The device is thus suitable for storing the monomer liquid 4 and the cement powder 5 as parent components of a bone cement paste 54 of the PMMA bone cement. The device is however also suitable and designed for mixing the bone cement paste 54 from the parent components and for delivering the mixed bone cement past 54.

In the monomer receptacle 2, a conveying plunger 6 made of plastic is arranged in the cylindrical interior chamber of the monomer receptacle 2, which is movable in the longitudinal direction. The conveying plunger 6 is arranged in the area of the rear side of the monomer receptacle 2. The glass ampoule 3 can be pressed together with the conveying plunger 6 in the monomer receptacle 2 and thereby splintered, whereby the conveying plunger 6 is pressed in the direction of the front side, i.e. in the direction of the cartridge 1. One the front side, the conveying plunger 6 has scrapers, with which splinters from the glass ampoule 3 are wiped from the interior wall of the monomer receptacle 2. For this purpose, the scrapers lie on the side of the interior wall of the interior chamber of the monomer receptacle 2.

In the interior chamber of the cartridge 1, a delivery plunger 7 made of plastic is arranged in its rear side. Behind the conveying plunger 6 and the rear side of the monomer receptacle 2, a compressed gas connection 8 is provided, with which a compressed gas cartridge 10 can be connected to the interior chamber of the monomer receptacle 2 as a compressed gas source, so that a compressed gas can flow from the compressed gas cartridge 10 behind the conveying plunger 6 into the interior chamber of the monomer receptacle 2 and drive forward the conveying plunger 6 by the gas pressure in the direction of the front side of the cartridge 1.

The delivery plunger 7 has a hollow cylinder 9 on its front side to extend the distance that the monomer liquid 4 most flow through the cement powder 5, until it reaches the interior wall of the cartridge 1. Additionally, the hollow cylinder 9 is used to separate the delivery plunger 7 from a delivery opening on the front side of the interior chamber of the cartridge 1 and to create a dead volume between the delivery plunger 7 and the front side of the interior chamber of the cartridge 1 when the delivery plunger 7 or the hollow cylinder 9 is pressed to the maximum degree onto the front side of the interior chamber of the cartridge 1. The hollow cylinder 9 is here formed in a rotationally symmetric manner and in the style of a tube piece. However, the hollow cylinder 9 can also have longitudinal cuts that run parallel to the cylinder axis of the hollow cylinder 9. The hollow cylinder 9 is planar on the front side.

In the interior chamber of the monomer receptacle 2, a bearing 12 made of foam is provided which serves to provide security during transportation and as a shock absorber for the glass ampoule 3. In this manner, it is to be prevented that the class ampoule 3 breaks open in an unwanted manner during shock or impact. The foam and thus the bearing 12 are permeable for gases.

The cartridge 1 and the monomer receptacle 2 are designed as a single part as a shared plastic part. The monomer receptacle 2 and the cartridge 1 are connected with each other in a manner that is liquid permeable for the monomer liquid 4 via a connection 14 in the delivery plunger 7. The connection 14 via the delivery plunger 7 opens up into the interior chamber of the cartridge 1 through a porous filter 16 that is impermeable for the cement powder 5 but permeable for the monomer liquid 4.

In the confluence to the connection 14, a filter 18 is arranged in the delivery plunger 7 with which the splinters of the glass ampoule 3 can be retained. Instead of the filter 18 or in addition to the filter 18, a screen can also be provided.

Several ventilation openings 20 are provided in the wall of the monomer receptacle 2 in the area of the rear side, through which the interior chamber of the monomer receptacle 2 can be sterilised with the aid of a sterilising gas such as ethylene oxide. The ventilation openings 20 are arranged directly adjacent to the conveying plunger 6 and to the compressed gas connection 8, so that the conveying plunger 6 and the compressed gas connection 8 directly move in front of the ventilation openings 20 and thus close the ventilation openings 20 when the conveying plunger 6 and the compressed gas connection 8 are moved in the direction of the cartridge 1. As a result, it is prevented that the monomer liquid 4 can escape through the ventilation openings 20 when the glass ampoule 3 is opened in the monomer receptacle 2.

The cylindrical conveying plunger 6 has an external circumference that matches the cylinder geometry of the interior chamber of the monomer receptacle 2 and is sealed against the interior wall of the monomer receptacle 2 in a liquid-tight and pressure-tight manner via two circumferential seals 26. Equally, an external insert of the compressed gas connection 8 is sealed in a pressure-tight manner via two external circumferential seals 27 against the interior wall of the monomer receptacle 2 and the external insert is sealed against an internal portion of the compressed gas connection 8 via an internal circumferential seal 27. Further, the delivery plunger 7 is sealed against the interior wall of the cartridge 1 in the liquid-tight manner via two circumferential seals 28. These seals 26, 27 serve to ensure that the gas pressure cannot escape from the compressed gas cartridge 10 and is available for driving forward the conveying plunger 6. The seals 28 serve to prevent an exit of monomer liquid 4 or of bone cement paste 54 in order to prevent contamination of the environment (of the operating theater and the user). The seals 26,27,28 can here consist of rubber.

On the front side of the cartridge 1, a connection 34 is provided in the form of an outer thread, onto which a cartridge head 60 is screwed as a completion of the cartridge 1. In the cartridge head 60, the delivery opening is formed and in the initial state (see FIGS. 1A and 1B) is closed with a closure 36 which is inserted in the delivery opening and closes said opening. The closure 36 is first opened to deliver the mixed bone cement paste 54 (see FIG. 1E and FIGS. 3A and 3B). The closure 36 is a porous filter that is impermeable for the cement powder 5 but permeable for gases and has a cylindrical form. The closure 36 is preferably made of Porex or another open-pored plastic.

On outer thread 34 on the front side of the cartridge 1, the cartridge head 60 is screwed, which comprises a line element 37 with a closure holder 38 for holding the closure 36. The closure holder 38 is formed according to a type of sleeve and has four bars 39 aligned in the longitudinal direction and rising into the closure holder 38. The bars 39 distance the closure 36 from the interior wall of the closer holder 38 when the closure 36 is pressed into the closure holder 38. In front of the closure holder 38, the line element tapers 37. In this area, four further bars 40 are arranged which form a stop 40 for the movement of the closure 36 and thus limit the movement of the closure 36 into the closure holder 38. Between the bars 39,40, a sufficiently free line cross-section is provided, so that a bone cement paste 54 produced from the parent components 4,5 (see FIGS. 1A, 1C, and 1D) can flow between the bars 39, the wall of the closure holder 38 and the inserted closure 36, as well as between the bars 40 in the front portion of the line element 37.

On the rear side of the monomer receptacle 2, a container 41 is screwed for the compressed gas cartridge 10. The container 41 comprises the compressed gas connection 8 on its front side, which faces towards the monomer receptacle 2. The compressed gas cartridge 10 is inserted from the rear side into the container 41 for the compressed gas cartridge 10 and the container 41 is closed with a lied on the rear side.

One the front side of the conveying plunger 6, protruding wedges 42 are arranged which enable punctiform or linear force application into the glass ampoule 3 and thus facilitate the breaking open of the glass ampoule 3. The wedges 42 are provided for splitting or breaking the glass ampoule 3 when driving forward the conveying plunger 6.

Through closure 36 which is designed as a porous filter, the interior of the cartridge 1 and the cement powder 5 can be sterilised with the aid of ethylene oxide, since the line element 37 is open and the closure 36 and the intermediate spaces between the powder particles of the cement powder 5 are permeable to air. At the same time, air can be pressed out of the monomer receptacle 2 through the cement powder 5, the closure 36 and the open line element 37, when the conveying plunger 6 is pressed in the direction of the monomer receptacle 2.

The cement powder 5 is enclosed in the cartridge 1, since all openings and connections 14 are impermeably closed for the cement powder 5 with the aid of the porous filters 16, 36. The content of the cartridge 1 can here by sterilised through evacuation and rinsing with ethylene oxide. As a result, the device is also suitable for the long-term storage of the cement powder 5. The ethylene oxide can be rinsed through the device in the state shown in FIG. 1A, since a continuous, gas-permeable connection is provided between the delivery opening in the cartridge head 60 and the ventilation openings 20. Following sterilization with ethylene oxide, the ventilation openings 20 are closed, whereby the container 41 for the compressed gas cartridge 10 is a gain screwed onto the monomer receptacle 2, so that the ventilation openings 20 are traversed from inside by the conveying plunger 6 and the external seals 27 on the insert of the compressed gas connection 8 and are thus sealed and closed. For this purpose, the compressed gas connection 8 or the container 41 for the compressed gas cartridge 10 has an inner thread 50 and the rear side of the monomer receptacle 2 has a matching outer thread 51. The ventilation openings 20 are arranged in the area of the outer thread 51.

The compressed gas connection 8 has a hollow needle 43 with which the compressed gas cartridge 10 is to be opened when this is pushed onto the hollow needle 43 with a membrane on its front side. Then compressed gas flows from the compressed gas cartridge 10 through the hollow needle 43 and a sterile filter 44 on the rear side of the monomer receptacle 2 behind the conveying plunger 6 into the interior chamber of the monomer receptacle 2.

In order to be able to conveniently screw the container 41 for the compressed gas cartridge 10 onto the monomer receptacle 2, wings 46 are arranged outside on the container 41 so that the container 41 can be manually screwed on the monomer receptacle 2 up to a stop in order to close the ventilation openings 20.

The compressed gas cartridge 10 can also be opened in the same manner. For this purpose, a wing screw head 48, which extends through a passage in the rear lid of the container 41 for the compressed gas cartridge 10, is affixed on the floor of the compressed gas cartridge 10. The compressed gas cartridge 10 has an outer thread on its front side facing towards the hollow needle 43, and the compressed gas connection 8 has a matching inner thread. With the wing screw head 48, the compressed gas cartridge 10 within the container 41 can be screwed deeper into the compressed gas connection 8 towards the front, so that the membrane on the front side of the compressed gas cartridge 10 is pierced by the hollow needle 43 and the compressed gas is available within the device (see FIGS. 1B to 1D).

Due to the pressure acting on the rear side of the conveying plunger 6, the conveying plunger 6 is pressed in the direction of the cartridge head 60 and the glass ampoule 3 is splintered between the conveying plunger 6 and the delivery plunger 7 and is opened as a result. The splinters 52 of the glass ampoule 3 are further compressed and the released monomer liquid 4 is pressed through the filter 18 or the screen, through the connections 14 in the delivery plunger 7 and through the porous filter 16 into the interior chamber of the cartridge 1 and thus into the cement powder 5. The delivery plunger 7 is here held by the cement powder 5, since the cement powder 5 is not flowable in a dry state. In the interior chamber of the cartridge 1, the monomer liquid 4 mixes with the cement powder 5, since in the cement powder 5 an additive is distributed which guides the monomer liquid 4 and thus distributes it in the cement powder 5 before the monomer liquid 4 reacts with the cement powder 5 and swells up such that a further dissemination of the monomer liquid 4 is prevented. In addition, the monomer liquid 4 can penetrate deep into the cement powder 5 along the hollow cylinder 9. In the interior chamber of the cartridge 1, the bone cement paste 54 is thus formed (see FIG. 1D).

The bone cement paste 54 produced with the device can be filled with the device into a syringe 53 with which the bone cement paste 54 can be applied by the user (the operator) on the patient. For this purpose, the bone cement paste 54 an be driven forwards out of the syringe 53 with a plunger 55 of the syringe 53.

On the front side of the interior chamber of the cartridge 1, a groove 56 is provided in the side interior wall, via which the gas pressure can be blown out of the interior chamber of the cartridge 1 and the interior chamber of the monomer receptacle 2 when the rear end of the conveying plunger 6 is pushed past the rear end of the groove 56 (see FIGS. 2, 3A, and 3B). The compressed gas on the rear side of the monomer receptacle 2 can then flow past the conveying plunger 6, the splinters 52 of the glass ampoule 3 and the delivery plunger 7 and escape through the delivery opening. As a result, the device becomes pressure-free and can be disposed of without risk.

In a closed state, the closure 36 is arranged in an insert 58 on the cartridge head 60, which protrudes into the interior chamber of the cartridge 1 and which is sealed with two circumferential seals 59 against the interior wall of the cartridge 1. The insert 58 here forms a stop for the hollow cylinder 9 on the front side of the delivery plunger 7 and thus for the delivery plunger 7.

FIGS. 1A to 1E show five schematic profile views of one embodiment of the device according to the invention over each other to clearly illustrate the procedure of a method according to the invention. For this purpose, FIGS. 3A and 3B show a section enlargement of FIG. 1E and FIG. 2 shows an external view of the device in the initial state. At the start of the method, the device is in the initial state, as shown in FIG. 1A. In this state, the device is sterilised. Then, the container 41 for the compressed gas cartridge 10 is screwed with the wings 46 onto the monomer receptacle 2 and as a result, the ventilation openings 20 (FIG. 1A) are closed. This state is shown in FIG. 1B.

Then, the compressed gas cartridge 10 is opened whereby the compressed gas cartridge 10 is screwed onto the hollow needle 43 with the swing head screw 48. This situation is shown in FIG. 1C.

Then, the main part of the method according to the invention begins:

The gas exiting from the compressed gas cartridge 10 flows through the sterile filter 44 and presses onto the conveying plunger 6, pressing it forward towards the cartridge 1. Through the compressed gas that continues to flow from the compressed gas cartridge 10 into the rear interior chamber of the monomer receptacle 2, the conveying plunger 6 is driven forward towards the cartridge 1. The bearing 12 is compressed and the conveying plunger 6 impacts on the head of the glass ampoule 3. Since the glass ampoule 3 lies on the front side on the delivery plunger 7, and the interior chamber of the monomer receptacle 2 further decreases in size, the glass ampoule 3 is broken. The monomer liquid 4 exits from the glass ampoule 3 into the interior chamber of the monomer receptacle 2. The delivery plunger 7 cannot be pushed from the glass ampoule 3 towards the closure 36, or cannot be pushed far, when the cement powder 5 is dry, i.e. is not moistened by the monomer liquid 4, since the dry cement powder 5 is not flowable and blocks a movement of the delivery plunger 7. This situation is shown in FIG. 1C from 1A. Remaining air from the monomer receptacle 2 is pushed out through the filter 18, the connection 14, the porous filter 16, through the intermediate spaces between the particles of the cement powder 5 through the closure 36 and from the line element 37 out of the device.

Only small splinters 52 are ultimately left from the glass ampoule 3, which are retained by the filter 18 and which remain in the tubular container. The monomer liquid 4 is pressed through the filter 18, the connection 14 and the porous filter 16 into the cement powder 5 and there begins to react with the cement powder 5 so that the bone cement paste 54 is formed from the mixture. Here, the monomer liquid 4 cannot directly flow from the porous filter 16 to the interior wall of the cartridge 1, since this is fully covered, or in the case of a slit hollow cylinder 9 us largely covered, by the hollow cylinder 9. As a result, the monomer liquid 4 is forced to forge a path through the cement powder 5. Monomer liquid bubbles or monomer liquid accumulations can thus be prevented.

The quantity of monomer liquid 4 is selected such that the cement powder 5 is moistened with the monomer liquid 4 up until the foremost tip of the cartridge 1, i.e., up until the closure 36. As soon as the mixture, in other words the bone cement paste 54 has been produced, the closure 36 is pressed forwards by the pressure acting on the delivery plunger 7 as a result of the bone cement paste 54 and into the closure holder 38, until the closure 36 hits the stop 40, where the movement of the closure 36 ends. This situation is shown in FIG. 1D. The bone cement paste 54 flows around the closure 36, whereby it flows through between the bars 39 and between the bars 40. Finally, the bone cement paste 54 exits on the front side of the device.

At the latest in this state (or preferably already when the compressed gas cartridge 10 is opened), a syringe 53 is provided which can hold the bone cement in paste 54. Through further driving forward of the conveying plunger 6, the shards 52 and the delivery plunger 7 arranged before them with the compressed gas, the bone cement paste 54 is driven out of the cartridge 1 and filled into the syringe 53 for further use. This situation is shown in FIG. 1E and FIGS. 3A and 3B.

Finally, the hollow cylinder 9 impacts the cartridge head 60 or the insert 58 in the cartridge head 60 on the front side of the interior chamber of the cartridge 1. Here, the groove 56 is opened up and the pressure on the rear side of the conveying plunger 6 escapes through the groove 56 and through the discharge opening in the cartridge head 60.

The hollow cylinder 9 has a height of 3 mm, preferably of 5 mm or greater, so that through the distance generated by it, it is guaranteed that the front side of the delivery plunger 7 is at a distance from the front side of the interior chamber of the cartridge 1, when the delivery plunger 7 is pressed forwards as far as possible. As a result, in the interior chamber of the cartridge 1, in the area delimited by the hollow cylinder 9, a dead volume is created which cannot be driven out of the cartridge 1 through the delivery opening and the line element 37.

In this dead volume, a portion of the bone cement paste 54 is now located, which possibly contains too great a proportion of monomer liquid 4. This portion of bone cement paste 54 cannot be pressed out of the dead volume out of the device. Through this construction, it is ensured that no bone cement paste 54 can be applied with the device with a changing consistency due to the changing composition.

Figure 9:
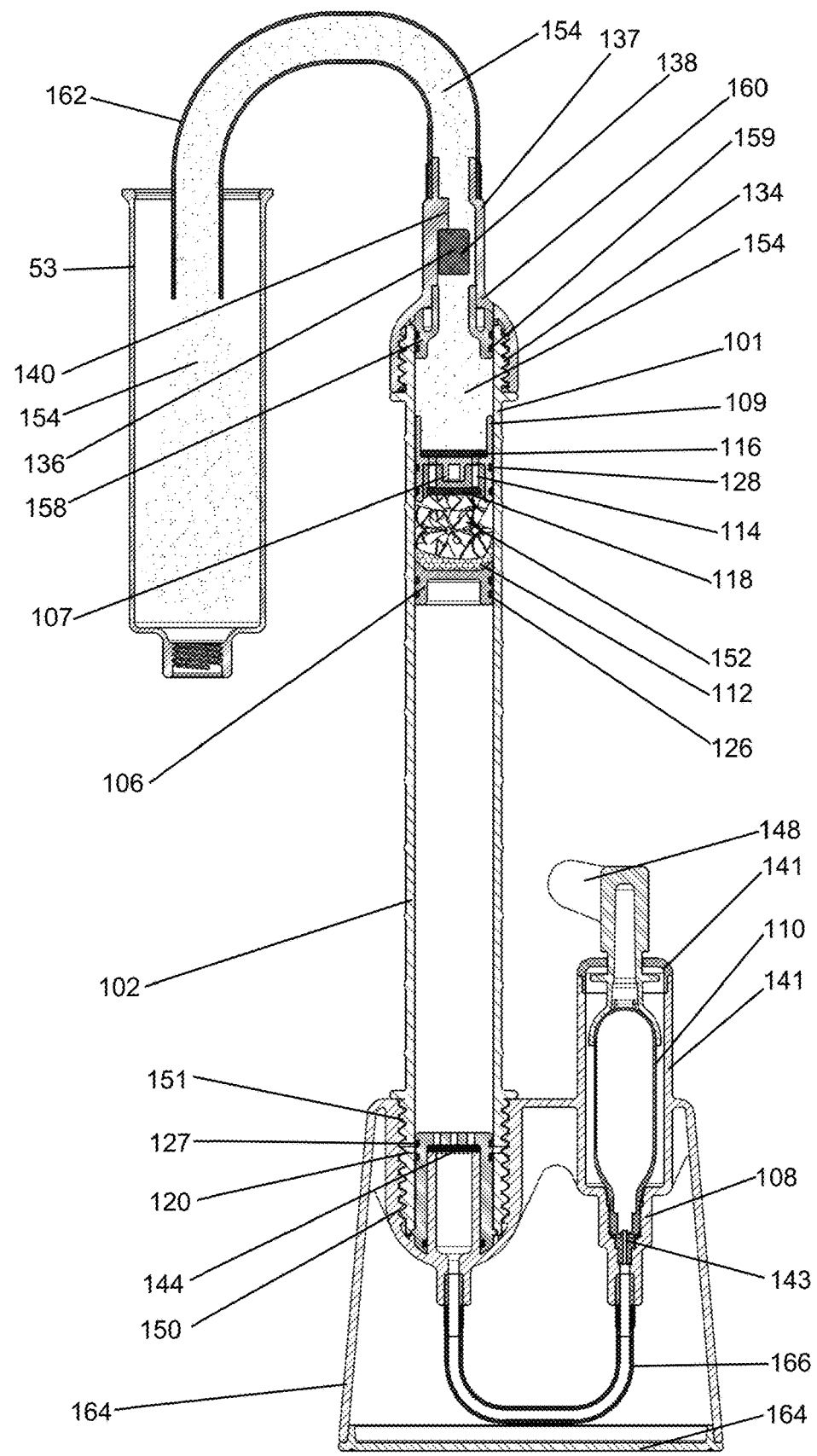
FIG. 9: shows a schematic profile view of the second device according to the invention according to FIGS. 4 to 8 with opened closure during delivery of the bone cement paste.
Figure 10A:
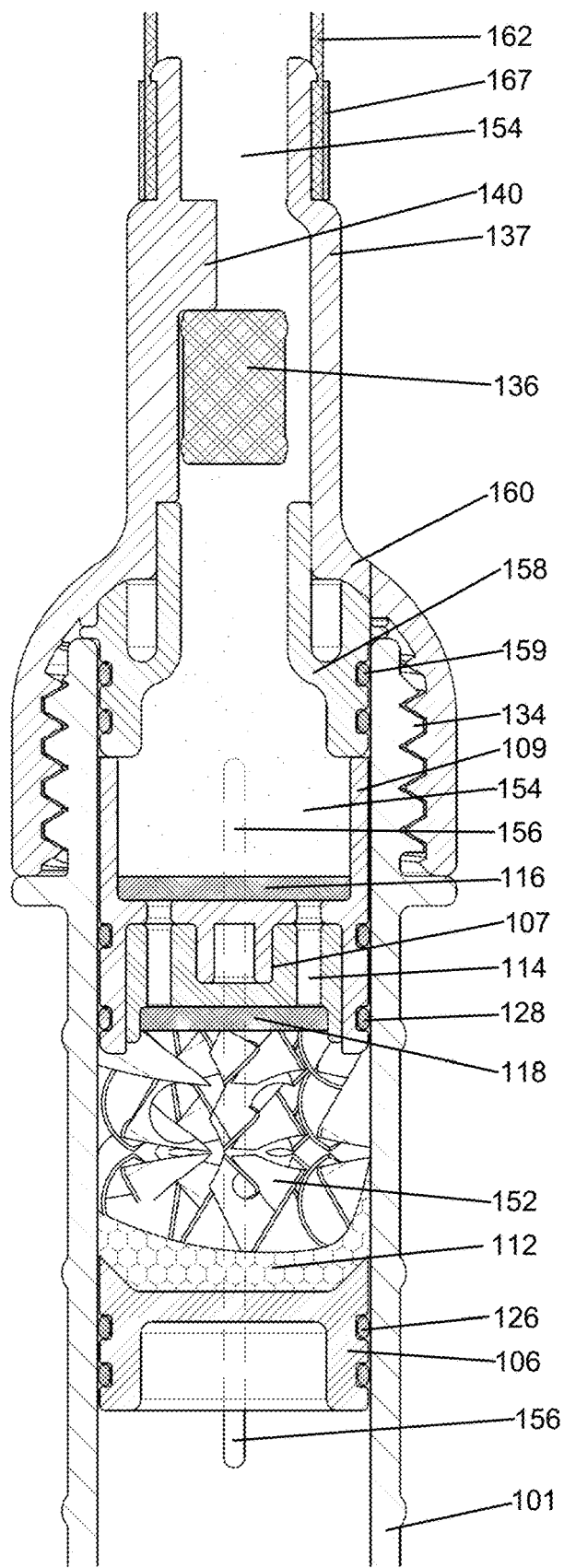
FIGS. 10A and 10B: show two schematic profile views as section enlargements of the second device according to FIGS. 4 to 9 adjacent to each other during pressing out of the bone cement paste, whereby the profile planes are vertical to each other.
Figure 10B:
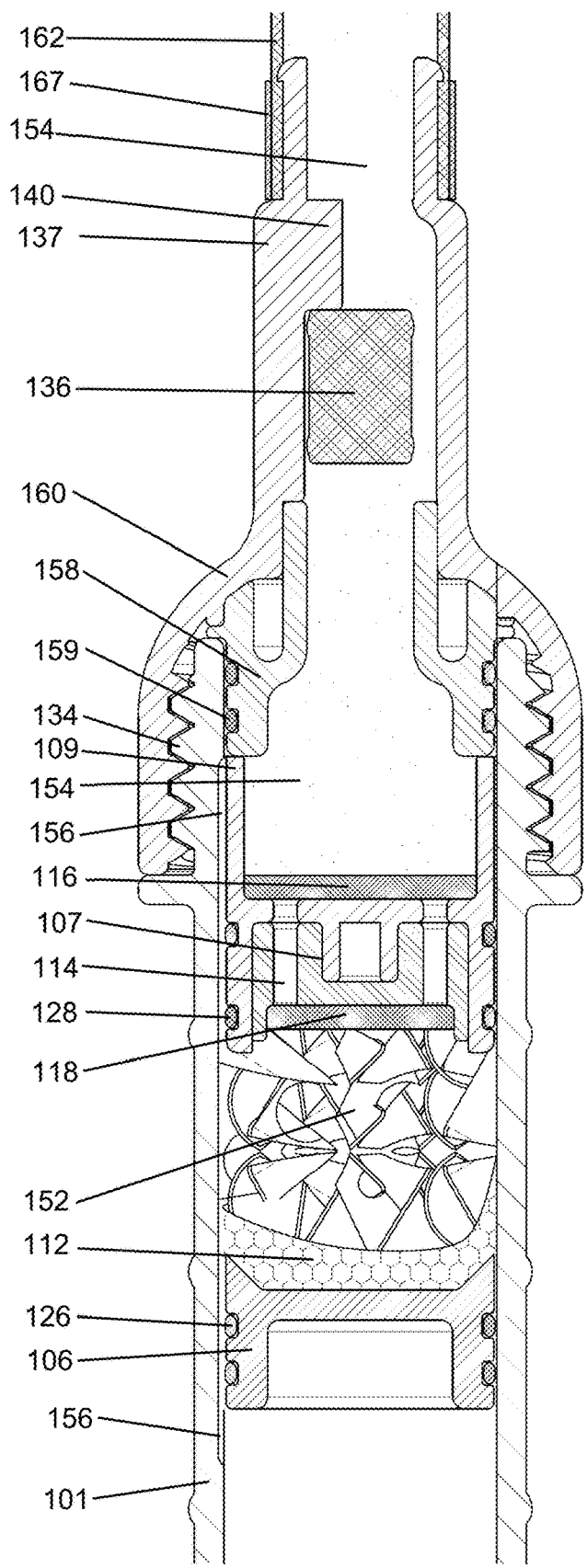

In FIGS. 4 to 10A and 10B, drawings of a second alternative device according to the invention are shown. FIGS. 4 to 9 show different schematic overall views of the exemplary second device according to the invention. FIGS. 10A and 10B show two schematic profile views as detailed views in the form of section enlargements through the front area of the second device according to the invention.

This second embodiment according to the invention differs from the first embodiment in that it is erectable and that the compressed gas connection is not directly placed on the monomer receptacle.

The second device according to the invention comprises, consists essentially of, or consists of a tubular container made of plastic, which as a front portion (in FIGS. 4 to 9 above) forms a cartridge 101 with a cylindrical interior chamber and which as a rear portion forms a monomer receptacle 102 for a glass ampoule 103 as a monomer liquid container. Instead of the plastic or glass ampoule 103, a tear-openable film bag made of a metal-coated plastic can also be used with slight conversion measures.

The rear side of the device is shown below in FIGS. 4 to 9. The tubular form of the container can easily be detected in the profile views and the perspective view according FIG. 4. Both the interior chamber of the cartridge 101 and the interior chamber of the monomer receptacle 102 are cylindrical with a circular base area. Here, the diameter of the interior chamber of the cartridge 101 and the diameter of the interior chamber of the monomer receptacle 102 are equally large and align. The container with the monomer receptacle 102 and the cartridge 101 is preferably made of plastic using the injection moulding technique. The monomer receptacle 102 thus has a cylindrical interior chamber into which the plastic or glass ampoule 103 is inserted. The monomer liquid 104 is located in the plastic or glass ampoule 103. In the interior chamber of the cartridge 101, a cement powder 105 form the parent components for a PMMA bone cement that is producible with the device. Due to the plastic or glass ampoule 103, the monomer liquid 104 can be stored for a very long period of time in the monomer receptacle 102 and as a result in the device. The cement powder 105 can also be stored for longer periods of time in the device. The device is thus suitable for storing the monomer liquid 104 and the cement powder 105 as parent components of a bone cement paste 154 of the PMMA bone cement. The device is however also suitable and designed for mixing the bone cement paste 154 from the parent components and for delivering the mixed bone cement paste 154.

In the cylindrical interior chamber of the monomer receptacle 102, a conveying plunger 106 that is movable in the longitudinal direction and which is made of plastic is arranged. The conveying plunger 106 is arranged in the area of the rear side of the monomer receptacle 102. The plastic or glass ampoule 103 can be pressed together with the conveying plunger 106 in the monomer receptacle 102 and thereby splintered, whereby the conveying plunger 106 is pressed in the direction of the front side, i.e. in the direction of the cartridge 101. On the front side, the conveying plunger 106 has scrapers, with which splinters 152 from the plastic or glass ampoule 103 are wiped from the interior wall of the monomer receptacle 102. For this purpose, the scrapers lie on the side of the interior wall of the interior chamber of the monomer receptacle 102.

In the interior chamber of the cartridge 101, a delivery plunger 107 made of plastic is arranged in its rear side. A compressed gas connection 108 is arranged at the side next to the monomer receptacle 102 and parallel to the monomer receptacle 102 in a stand 164. The stand 164 has a planar underside, so that the device can be erected on a planar subsurface, such as a table. Above the stand 164, the monomer receptacle 102 is arranged with the cartridge 101 next to the compressed gas connection 108. The compressed gas connection 108 is connected with the conveying plunger 106 and the rear side of the monomer receptacle 102 in a gas-permeable manner via a compressed gas line 166. With the compressed gas connection 108 and via the compressed gas line 166, a compressed gas cartridge 110 can be connected to the interior chamber of the monomer receptacle 102 as a compressed gas cartridge 110 behind the conveying plunger 106 into the interior chamber of the monomer receptacle 102 and drive forward the conveying plunger 106 by the gas pressure in the direction of the frond side of the cartridge 101.

The delivery plunger 107 has a hollow cylinder 109 on its front side to extend the distance that the monomer liquid 104 must flow through the cement powder 105, until it reaches the interior wall of the cartridge 101. Additionally, the hollow cylinder 109 is used to separate the delivery plunger 107 from a delivery opening on the front side of the interior chamber of the cartridge 101 and to create a dead volume between the delivery plunger 107 and the front side of the interior chamber of the cartridge 101 when the deliver plunger 107 or the hollow cylinder 109 is pressed to the maximum degree onto the front side of the interior chamber of the cartridge 101. The hollow cylinder 109 is here formed in a rotationally symmetric manner and in the style of a lit tube piece. For this purpose, the hollow cylinder 109 has longitudinal cuts that run parallel to the cylinder axis of the hollow cylinder 109.

In the interior chamber of the monomer receptacle 102, a bed 112 made of foam is provided which serves to provide security during transportation and as a shock absorber for the plastic or glass ampoule 103. In this manner, it is to be prevented that the plastic or glass ampoule 103 breaks open in an unwanted manner during shock or impact.

The cartridge 101 and the monomer receptacle 102 are designed as a single part as a shared plastic part. The monomer receptacle 102 and the cartridge 101 are connected with each other in a manner that is liquid permeable for the monomer liquid 104 via a connection 114 in the deliver plunger 107. The connection 114 via the delivery plunger 107 opens p into the interior chamber of the cartridge 101 through a porous filter 116 that is impermeable for the cement powder 105 but permeable for the monomer liquid 104.

In the confluence to the connection 114, a filter 118 is arranged in the delivery plunger 107 with which the splinters 152 of the plastic or glass ampoule 103 can be retained. Instead of the filter 118 or in addition to the filter 118, a screen can also be provided.

Several ventilation openings 120 are provided in the wall of the monomer receptacle 102 in the area of the rear side, through which the interior chamber of the monomer receptacle 102 can be sterilised with the aid of a sterilising gas such as ethylene oxide. The ventilation openings 120 are arranged directly adjacent to the conveying plunger 106 and to an insert with circumferential seals 127, so that the conveying plunger 106 and the insert with the seals 127 directly move in front of the ventilation openings 120 and thus close the ventilation openings 120 when the conveying plunger 106 and the insert with the seals 127 are moved in the direction of the cartridge 101, whereby the monomer receptacle 102 is screwed into the stand 164 with an inner thread 150. For this purpose, the monomer receptacle 102 is screwed into the stand 164 with an inner thread 150. For this purpose, the monomer receptacle 102 has an outer thread 151 on the rear side. Through the closure of the ventilation openings 120, it is prevented that the monomer liquid 104 can escape through the ventilation openings 120 when the plastic or glass ampoule 103 is opened in the monomer receptacle 102.

The cylindrical conveying plunger 106 has an external circumference that matches the cylinder geometry of the interior chamber of the monomer receptacle 102 and is sealed against the interior wall of the monomer receptacle 102 in a liquid-tight and pressure-tight manner via two circumferential seals 126. Equally, the insert is sealed in a pressure-tight manner via two circumferential seals 126. Equally, the insert is sealed in a pressure-tight manner via two external circumferential seals 127 against the interior wall of the monomer receptacle 102 and the insert is sealed against a confluence of the compressed gas line 166 via an internal circumferential seal 127. Further, the delivery plunger 107 is sealed against the interior wall of the cartridge 101 in the liquid-tight manner via two circumferential seals 128. These seals 126, 127 serve to ensure that the gas pressure cannot escape from the compressed gas cartridge 110 and is available for driving forward the conveying plunger 106. The seals 128 serve to prevent an exit of monomer liquid 104 or of bone cement paste 154 in order to prevent contamination of the environment (of the operating theater and the user). The seals 126, 127, 128 can consist of rubber.

On the front side of the cartridge 101, a connection 134 is provided in the form of an outer thread, onto which a cartridge head 160 is screwed as a completion of the cartridge 101. In the cartridge head 160, the delivery opening is formed and in the initial state (see the FIGS. 5 and 6) is closed with a closure 136 which is inserted in the delivery opening and closes said opening. The closure 136 is first opened to deliver the mixed bone cement paste 154 (see FIGS. 9, 10A, and 10B). The closure 136 is a porous filter that is impermeable for the cement powder 105 but permeable for gases and has a cylindrical form. The closure 136 is preferably made of Porex or another open-pored plastic On the outer thread 134 on the front side of the cartridge 101, the cartridge head 160 is screwed, which comprises a line element 137 with a closure holder 138 for holding the closure 136. The closure holder 138 is formed according to a type of sleeve and has four bars 139 aligned in the longitudinal direction and rising into the closure holder 138. The bars distance the closure 136 from the interior wall of the closure holder 138 when the closure 136 is pressed into the closure holder 138. In front of the closure holder 138, the line element tapers 137. In this area, four further bars 140 are arranged which form a stop 140 for the movement of the closure 136 and thus limit the movement of the closure 136 into the closure holder 138. Between the bars 139,140, a sufficiently free line cross-section is provided, so that a bone cement paste 154 produced from the parent components 104, 105 (see FIGS. 8 and 9) can flow between the bars 139, the wall of the closure holder 138 and the inserted closure 136, as well as between the bars 140 in the front portion of the line element 137.

On the front side of the cartridge head 160, a tube 162 is affixed with a crimping sleeve 167, via which the bone cement paste 154 can be filled. For this purpose, the tube 162 has a bend so that the bone cement paste 154 is delivered downwards when erected with the stand 164 on a horizontal subsurface, such as a table (see FIG. 9). Through the gravitation, the bone cement paste 154 can then run out below.

On the stand 164, a container 141 is formed for the compressed gas cartridge 110. The container 141 for the compressed gas cartridge 110 is here largely formed from plastic as a single-part injection moulded part together with the stand 164. The container 141 comprises the compressed gas connection 108 on its front side, which faces towards the compressed gas line 166. The compressed gas cartridge 110 is inserted from the rear side into the container 141 for the compressed gas cartridge 110 and the container 141 is closed with a lid on the rear side.

On the front side of the conveying plunger 106, protruding wedges 142 are arranged which enable punctiform or linear force application into the plastic or glass ampoule 103 and thus facilitate the breaking open of the plastic or glass ampoule 103. The wedges 142 are provided for splitting or breaking the plastic or glass ampoule 103 when driving forward the conveying plunger 106.

Through the closure 136 which is designed as a porous filter, the interior of the cartridge 101 and the cement powder 105 can be sterilised with the aid of ethylene oxide, since the line element 137 is open and the closure 136 and the intermediate spaces between the powder particles of the cement powder 105 are permeable to air. At the same time, air can be pressed out of the monomer receptacle 102 through the cement powder 105, the closure 136 and the open line element 137, when the conveying plunger 106 is pressed in the direction of the monomer receptacle 102.

Figure 4:
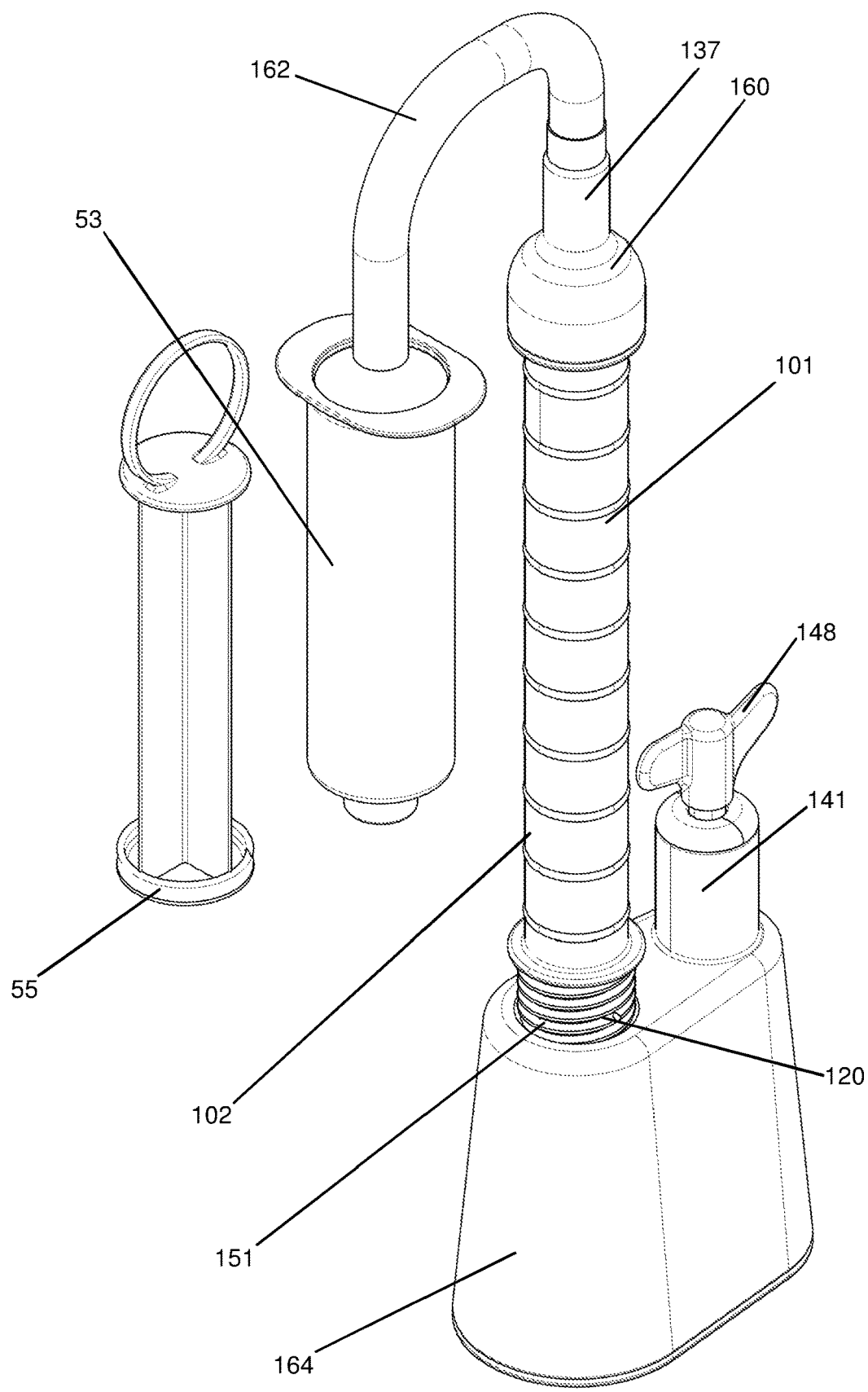
FIG. 4: shows a schematic perspective external view of a second device with a syringe for applying the bone cement paste.
Figure 5:
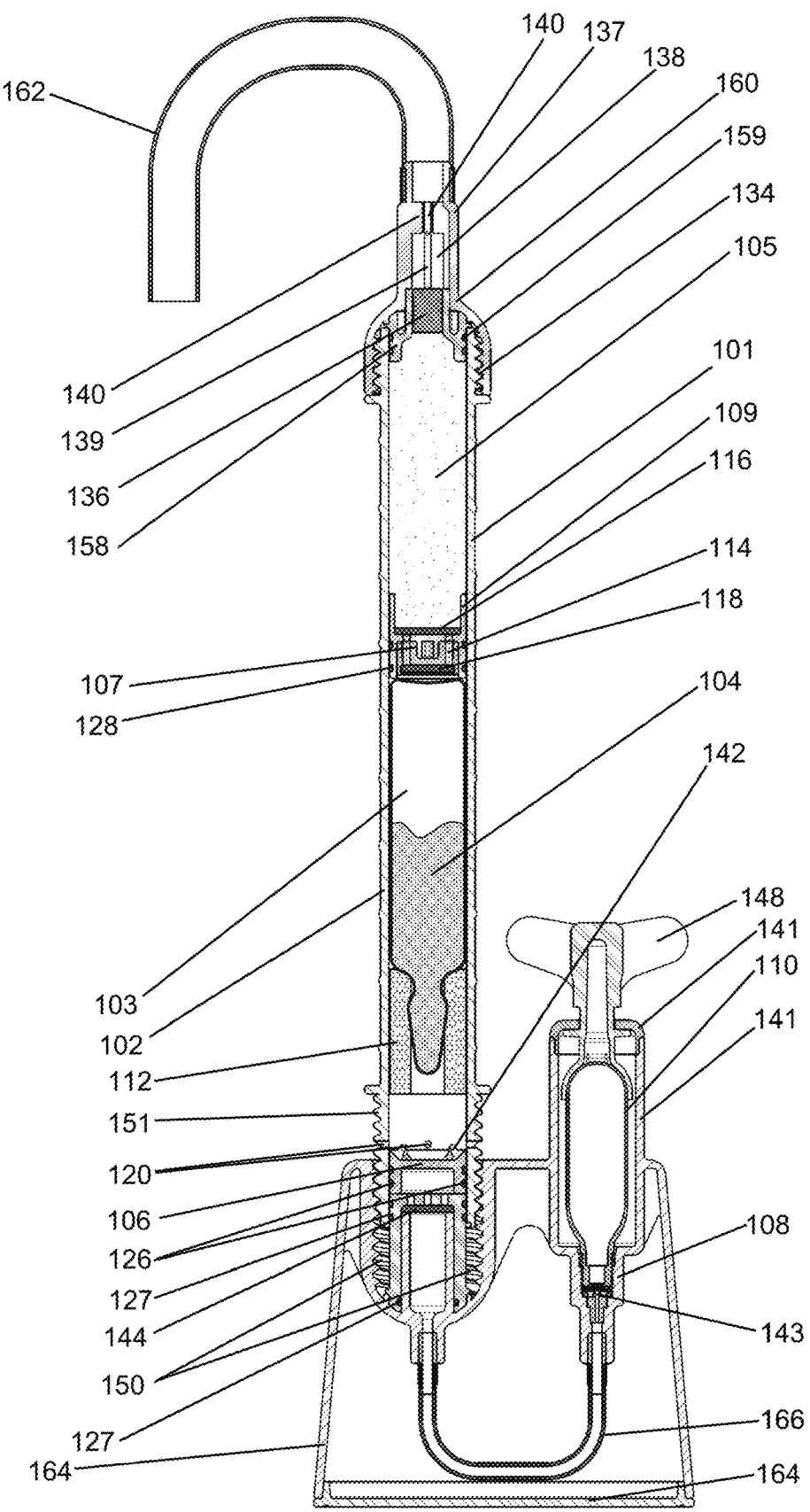
FIG. 5: shows a schematic profile view of the second device according to the invention according to FIG. 4 with opened ventilation openings.

The cement powder 105 is enclosed in the cartridge 101, since all openings and connections 114 are impermeably closed for the cement powder 105 with the aid of the porous filters 116, 136. The content of the cartridge 101 can here be sterilised through evacuation and rinsing with ethylene oxide. As a result, the device is also suitable for the long-term storage of the cement powder 105. In FIGS. 4 and 5, the ethylene oxide can be rinsed through the device, since a continuous, gas-permeable connection is provided between the delivery opening in the cartridge head 160 and the ventilation openings 120. Following sterilization with ethylene oxide, the ventilation openings 120 are closed, whereby the monomer receptacle 102 is further screwed into the stand 164 and as a result is screwed onto the insert with the seals 127, so that the ventilation openings 120 are traversed from inside by the conveying plunger 106 and the external seals 127 on the insert and are thus sealed and closed. For this purpose, the stand 164 has the inner thread 150 and the rear side of the monomer receptacle 102 has the matching outer thread 151. The ventilation openings 120 are arranged in the area of the outer thread 151.

The compressed gas connection 108 has a hollow needle 143 with which the compressed gas cartridge 110 is to be opened when this is pushed onto the hollow needle 143 with a membrane on its front side. Then the compressed gas flows from the compressed gas cartridge 110 through the hollow needle 143, the compressed gas line 166 and a sterile filter 144 into the rear side of the interior chamber of the monomer receptacle 102 behind the conveying plunger 106.

The compressed gas cartridge 110 can be opened, whereby a wing screw head 148 is turned, which extends through a passage in the rear lid of the container 141 for the compressed gas cartridge 110 and is affixed on the floor of the compressed gas cartridge 110. The compressed gas cartridge 110 has an outer thread on its front side facing towards the hollow needle 143, and the compressed gas connection 108 has a matching inner thread. With the wing screw head 148, the compressed gas cartridge 110 within the container 141 can be screwed deeper into the compressed gas connection 108 towards the front, so that the membrane on the front side of the compressed gas cartridge 110 is pierced by the hollow needle 143 and the compressed gas Is available within the device.

Due to the pressure acting on the rear side of the conveying plunger 106, the conveying plunger 106 is pressed in the direction of the cartridge head 160 and the plastic or glass ampoule 103 is splintered between the conveying plunger 106, and the delivery plunger 107 and is opened as a result. The splinters 152 of the plastic or glass ampoule 103 are further compressed and the released monomer liquid 104 is pressed through the filter 118, through the connections 114 in the delivery plunger 107 and through the porous filter 116 into the interior chamber of the cartridge 101 and thus into the cement powder 105. The delivery plunger 107 is here held by the cement powder 105, since the cement powder 105 is not flowable in a dry state. In the interior chamber of the cartridge 101, the monomer liquid 104 mixes with the cement powder 105, since the cement powder 105 and additive is distributed which guides the monomer liquid 104 and thus distributes it in the cement powder 105 before the monomer liquid 104 reacts with the cement powder 1105 and swells up such that a further dissemination of the monomer liquid 104 is prevented. In addition, the monomer liquid 104 can penetrate deep into the cement powder 105 along the hollow cylinder 109. In the interior chamber of the cartridge 101, the bone cement paste 154 is thus formed (see FIG. 8).

The bone cement paste 154 produced with the device can be filled with the device into a syringe 53 with which the bone cement paste 154 can be applied by the user (the operator) on the patient. For this purpose, the bone cement paste 154 can be driven forwards out of the syringe 53 with a plunger 55 of the syringe 53.

On the front side of the interior chamber of the cartridge 101, a groove 156 is provided in the side interior wall, via which the gas pressure can be blown out of the interior chamber of the cartridge 101 and the interior chamber of the monomer receptacle 102 when the rear end of the conveying plunger 106 is pushed past the rear end of the groove 156 (see FIGS. 9, 10A, and 10B). The compressed gas on the rear side of the monomer receptacle 102 can then flow past the conveying plunger 106, the splinters 152 of the plastic or glass ampoule 103 and the delivery plunger 107 and escape through the delivery opening. As a result, the device becomes pressure-free and can be disposed of without risk.

In a closed state, the closure 136 is arranged in an insert 158 on the cartridge head 160, which protrudes at the front into the interior chamber of the cartridge 101 and which is sealed with two circumferential seals 159 against the interior wall of the cartridge 101. The insert 158 here forms a stop for the hollow cylinder 109 on the front side of the delivery plunger 107 and thus for the delivery plunger 107.

Figure 6:
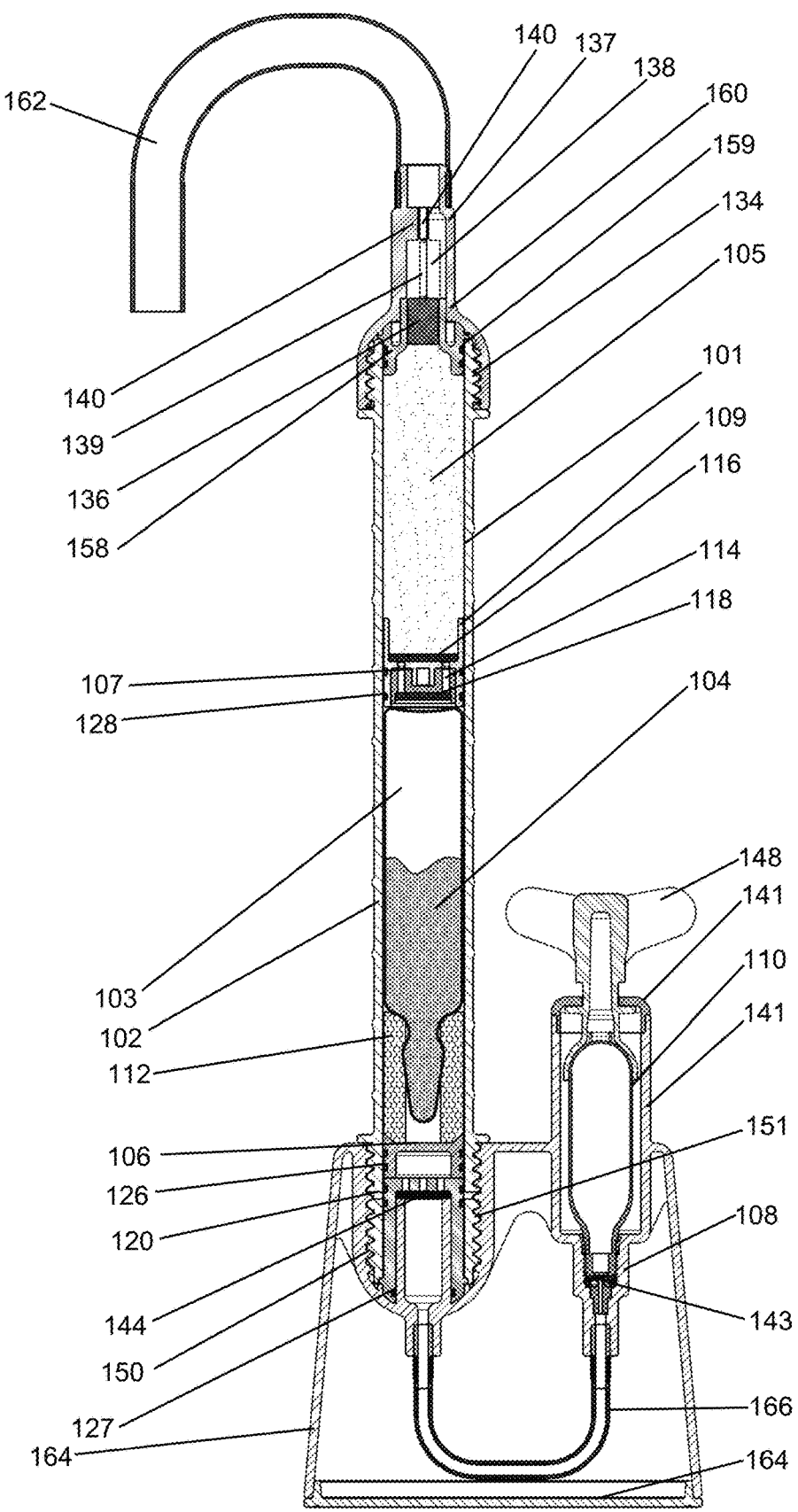
FIG. 6: shows a schematic profile view of the second device according to the invention according to FIGS. 4 and 5 and with closed ventilation openings.

FIGS. 5 to 9 show five schematic profile views of one embodiment of the device according to the invention to clearly illustrate the procedure of a method according to the invention. For this purpose, FIGS. 10A and 10B show a section enlargement of FIG. 9 and FIG. 4 shows an external view of the device in the initial state. At the start of the method, the device is in the initial state, as shown FIGS. 4 and 5. In this state, the device is sterilised. Then, the monomer receptacle 102 is screwed into the stand 164 and as a result, the ventilation openings 120 are closed. This state is shown in FIG. 6.

Figure 7:
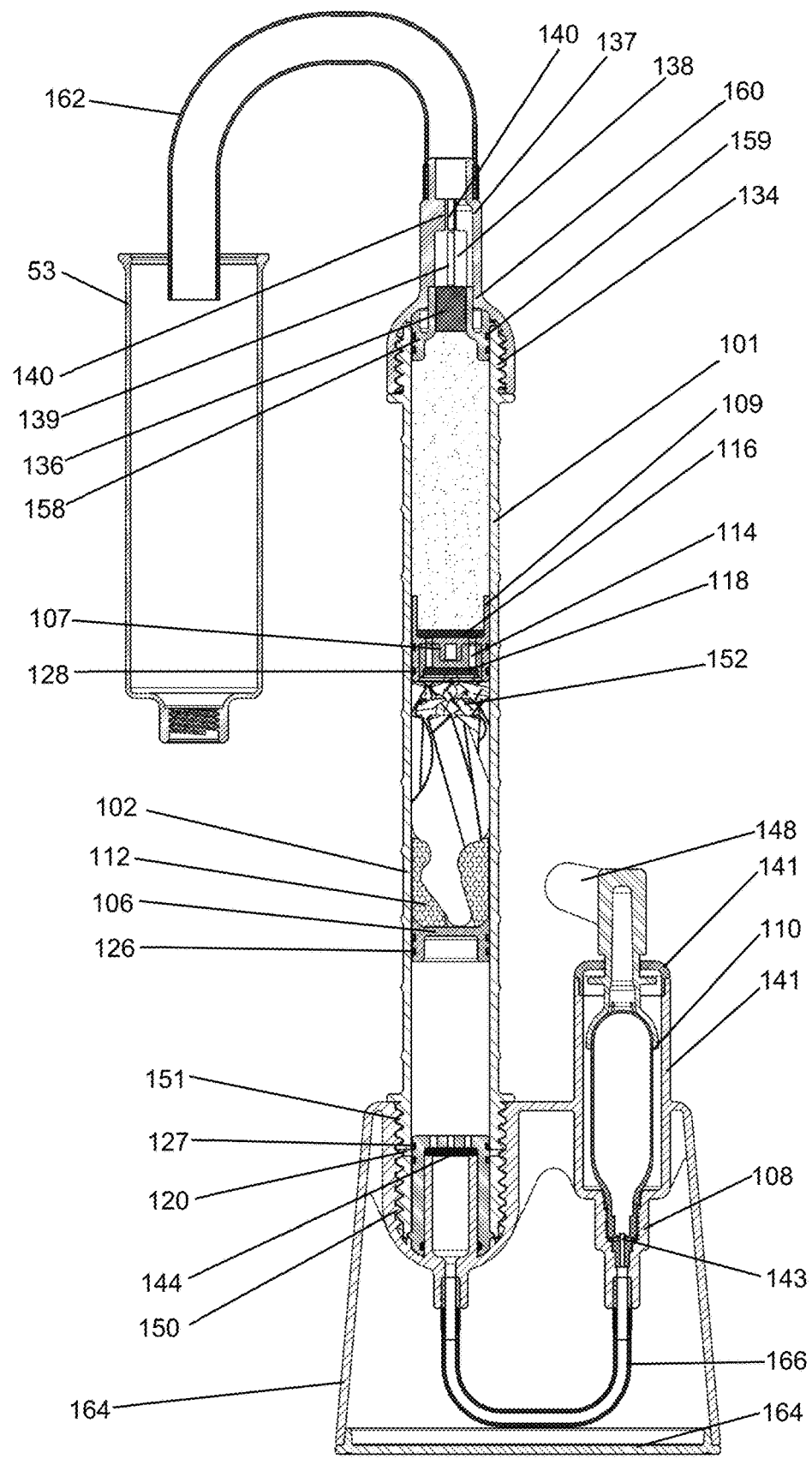
FIG. 7: shows a schematic profile view of the second device according to the invention according to FIGS. 4 to 6 with an opened gas cartridge and with opened glass ampoule.
Figure 8:
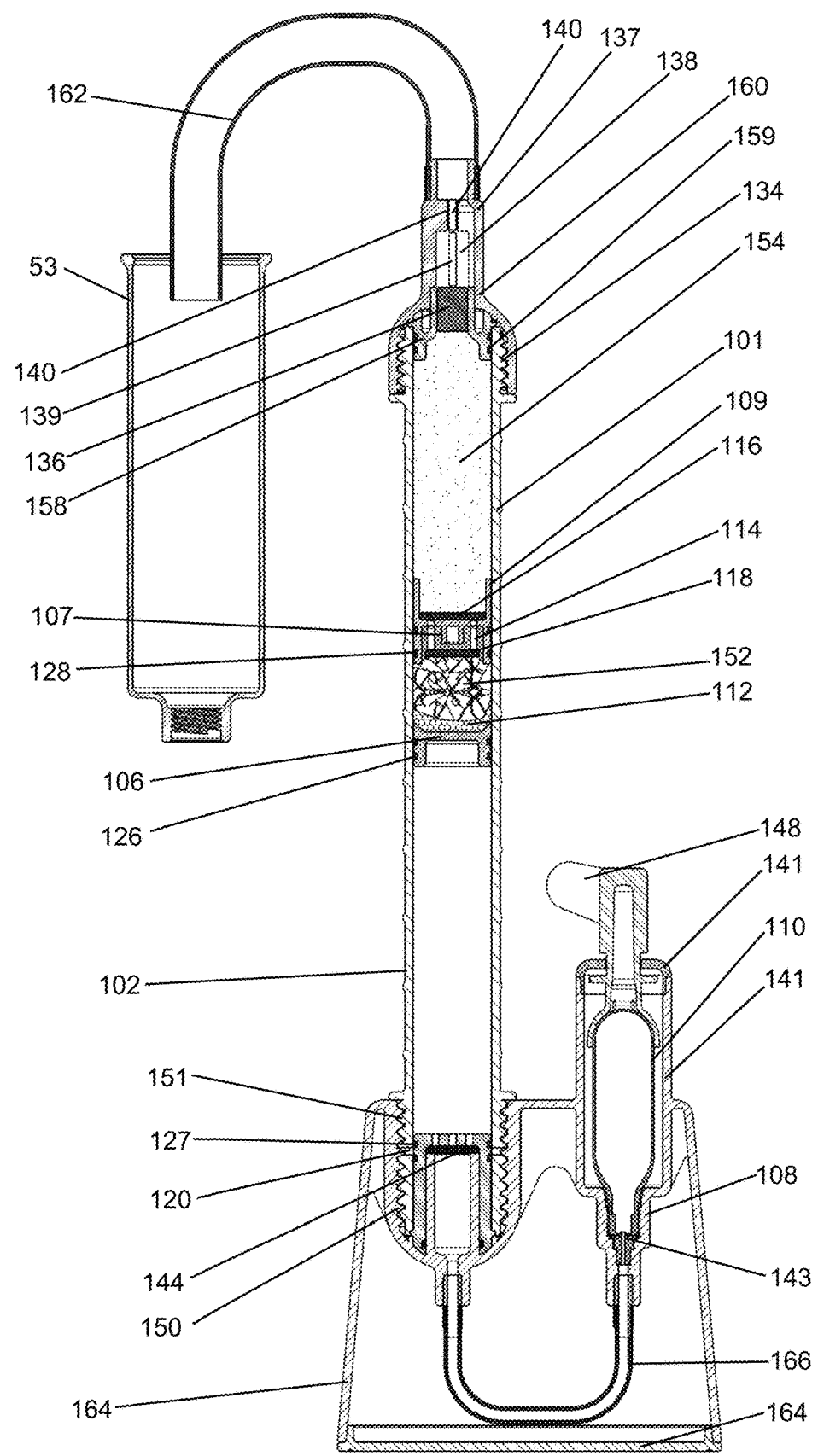
FIG. 8: shows a schematic profile view of the second device according to the invention according to FIGS. 4 to 7 with a fully compressed glass ampule.

Then, the compressed gas cartridge 110 is opened whereby the compressed gas cartridge 110 is screwed onto the hollow needle 143 with the wing head screw 148. This situation is shown in FIG. 7.

Then, the main part of the method according to the invention begins.

The gas exiting from the compressed gas cartridge 110 flows through the compressed gas line 166 and through the sterile filter 144 and presses onto the conveying plunger 106, pressing it forward towards the cartridge 101. Through the compressed gas that continues flow from the compressed gas cartridge 110 into the rear interior chamber of the monomer receptacle 102, the conveying plunger 106 is driven forward towards the cartridge 101. The bearing 112 is compressed and the conveying plunger 106 impacts on the head of the plastic or glass ampoule 103. Since the plastic or glass ampoule 103 lies on the front side on the delivery plunger 107, and the interior chamber of the monomer receptacle 102 further decreases in size, the plastic or glass ampoule 103 is broken. The monomer liquid 104 exits from the plastic or glass ampoule 103 into the interior chamber of the monomer receptacle 102. The delivery plunger 107 cannot be pushed from the plastic or glass ampoule 103 towards the closure 136, or cannot be pushed far, when the cement powder 105 is dried, i.e. is not moistened by the monomer liquid 104, since the dry cement powder 105 is not flowable and blocks a movement of the delivery plunger 107. This situation is shown in FIG. 7. Remaining air from the monomer receptacle 102 is pushed out through the filter 118, the connection 114, the porous filter 116, through the intermediate spaces between the particles of cement powder 105, through the closure 136 and from the line element 137 out of the device.

Only small splinters 152 are ultimately left from the plastic or glass ampoule 103, which are retained by the filter 118 and which remain in the tubular container. The monomer liquid 104 is pressed through the filter 118, the connection 114 and the porous filter 116 into the cement powder 105 and there begins to react with the cement powder 105, such that the bone cement paste 154 forms from the mixture. Here, the monomer liquid 104 cannot directly flow from the porous filter 116 to the interior wall of the cartridge 101, since this is covered by the slit hollow cylinder 109. As a result, the monomer liquid 104 is forced to forge a path through the cement powder 105. Monomer liquid bubbles or monomer liquid accumulations can thus be prevented.

The quantity of monomer liquid 104 is selected such that the cement powder 105 is moistened with the monomer liquid 104 up until the foremost tip of the cartridge 101, i.e. up until the closure 136. As soon as the mixture, in other words the bone cement paste 154 has been produced, the closure 136 is pressed forwards by the pressure acting on the delivery plunger 107 as a result of the bone cement paste 154 and into the closure holder 138, until the closure 136 hits the stop 140, where the movement of the closure 136 ends. This situation is shown in FIGS. 9, 10A, and 10B. The bone cement paste 154 flows around the closure 136, by flowing through between the bars 139 and between the bars 140. Finally, the bone cement paste 154 exits on the front side of the device through the tube 162.

At the latest in this state (or preferably already when the compressed gas cartridge 110 is opened), a syringe 53 is provided which can hold the bone cement paste 154. Through further driving forward of the conveying plunger 106, the shards 152 and the delivery plunger 107 arranged before them with the compressed gas, the bone cement paste 154 is driven out of the cartridge 101 and filled into the syringe 53 for further use. This situation is shown in FIGS. 9, 10A, and 10B.

Finally, the hollow cylinder 109 impacts the cartridge head 160 or the insert 158 in the cartridge head 160 on the front side of the interior chamber of the cartridge 101. Here, the groove 156 is opened up and the pressure on the rear side of the conveying plunger 106 escapes through the groove 156 and through the discharge opening in the cartridge head 160.

The hollow cylinder 109 has a height of 3 mm, preferably of 5 mm or greater, so that through the distance generated by it, it is guaranteed that the front side of the delivery plunger 107 is at a distance from the front side of the interior chamber of the cartridge 101, when the delivery plunger 107 is pressed forwards as far as possible. As a result, in the interior chamber of the cartridge 101, in the area delimited by the hollow cylinder 109, a dead volume is created which cannot be driven out of the cartridge 101 through the delivery opening, the line element 137 and the tube 162.

In this dead volume, a portion of the bone cement paste 154 is now located, which possibly contains too great a proportion of monomer liquid 104. This portion of bone cement paste 154 cannot be pressed out of the dead volume out of the device. Through this construction, it is ensured that no bone cement paste 154 can be applied with the device with a changing consistency due to the changing composition.

Figure 11:
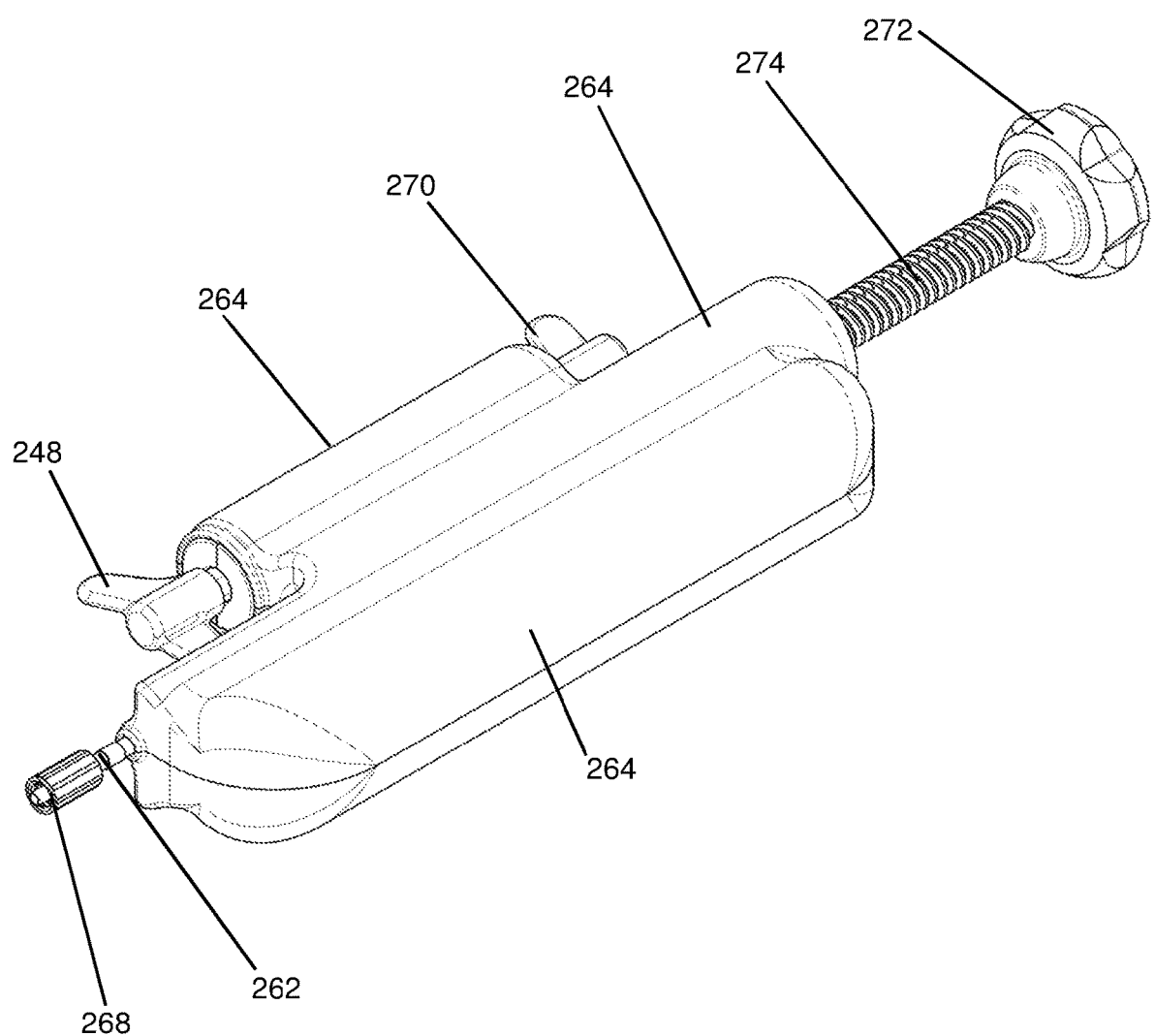
FIG. 11: shows a schematic perspective external view of a third device according to the invention.

In FIGS. 11 to 13, 14A to 14B, and 15A to 15B, drawings of a third alternative device according to the invention are shown. FIGS. 11 to 13, 14A to 14B, and 15A to 15B show different schematic overall views of the exemplary second device according to the invention. In FIG. 11, the third device is shown from outside with a closed housing 264, in FIG. 12 with an open housing 264 and in FIGS. 13, 14A to 14B, and 15A to 15B, profile views of the device during the procedure of a method according to the invention are shown.

The first device according to the invention comprises a cartridge 201 with a cylindrical interior chamber and a monomer receptacle 202 for a glass ampoule 203 as a monomer liquid container. Instead of the glass ampoule 203, a plastic container can be used, or, with slight conversion measures, also a tear-openable film bag made of a metal-coated plastic.

Both the interior chamber of the cartridge 201 and the interior chamber of the monomer receptacle 202 are cylindrical with a circular base area. The monomer receptacle 202 and the cartridge 201 are preferably made of plastic using the injection moulding technique. The monomer receptacle 202 thus has a cylindrical interior chamber into which the glass ampoule 203 is inserted. The monomer liquid 204 is located in the glass ampoule 203. In the interior chamber of the cartridge 201, a cement powder 205 is filled in or preferably pressed in. The monomer liquid 204 and the cement powder 205 form the parent components for a PMMA bone cement that is producible with the device. Due to the glass ampoule 203, the monomer liquid 204 can be stored for a very long period of time in the monomer receptacle 202 and as a result in the device. The cement powder 205 can also be stored for longer periods of time in the device. The device is thus suitable for storing the monomer liquid 204 and the cement powder 205 as parent components of a bone cement paste 254 of the PMMA bone cement. The device is however also suitable and designed for mixing the bone cement paste 254 from the parent components and for delivering the mixed bone cement paste 254.

In the cylindrical interior chamber of the monomer receptacle 202, a conveying plunger 206 made of plastic that is movable in the longitudinal direction is arranged. The conveying plunger 206 is arranged in the area of the rear side of the monomer receptacle 202 (in FIGS. 12 and 13 below and in FIGS. 14A, 14B, 15A, and 15B on the left). The glass ampoule 203 can be pressed together with the conveying plunger 206 in the monomer receptacle 202 and thereby splintered, whereby the conveying plunger 206 is pressed in the direction of the front side of the monomer receptacle 202. On the front side, the conveying plunger 206 has scrapers, with which splinters 252 from the glass ampoule 203 are wiped from the interior wall of the monomer receptacle 202. For this purpose, the scrapers lie on the side of the interior wall of the interior chamber of the monomer receptacle 202.

Figure 12:
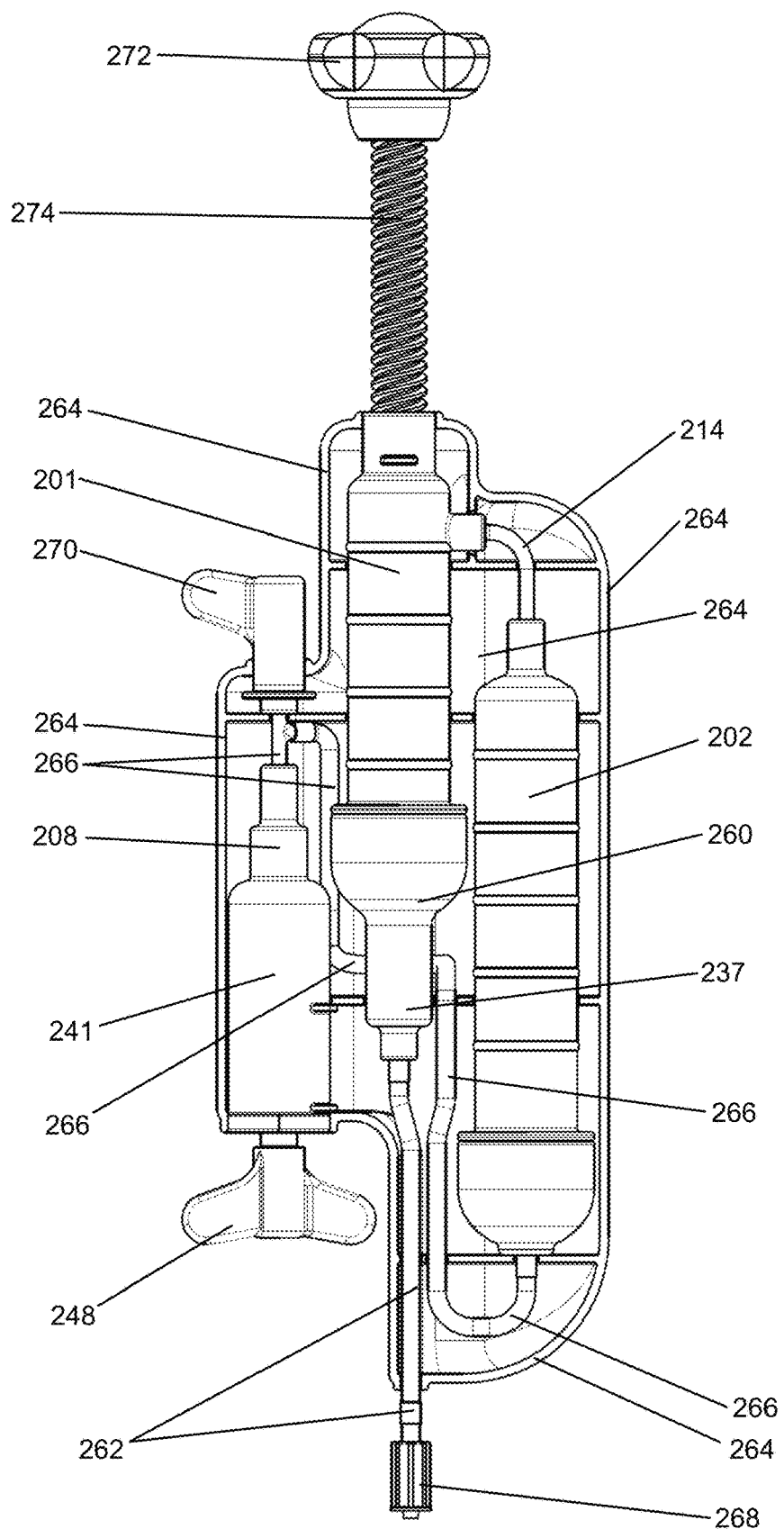
FIG. 12: shows a schematic profile view of the third device according to the invention according to FIG. 11 with opened housing.
Figure 13:
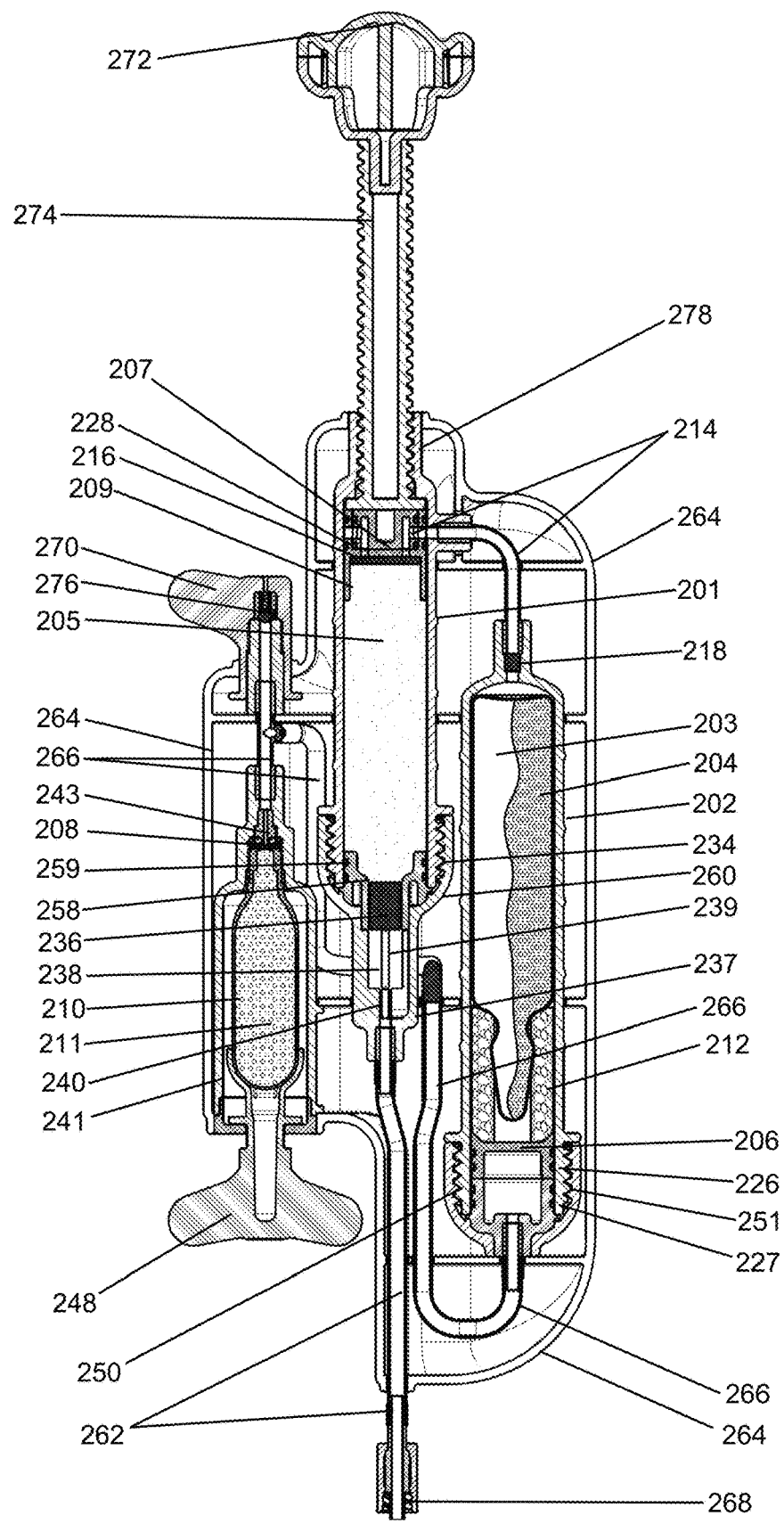
FIG. 13: shows a schematic profile view of the third device according to the invention according to FIGS. 11 and 12 in the initial state.

In the interior chamber of the cartridge 201, a delivery plunger 207 made of plastic is arranged in its rear side (in FIGS. 12 and 13 above and in FIGS. 14A, 14B, 15A, and 15B on the right). A compressed gas connection 208 is arranged at the side next to the cartridge 201 and parallel to the cartridge 201 in a housing 264. The housing 264 closes the cartridge 201, the monomer receptacle 202, the compressed gas connection 208 and further parts of the device from the outside. Above the stand 264, the monomer receptacle 202 is arranged and held with the cartridge 201 and the compressed gas connection 208 next to each other. The cartridge 201 and the monomer receptacle 202 are connected to each other in a liquid-permeable manner via a connection 214 in the form of a line 214 and a passage 214 through the delivery plunger 207. The compressed gas connection 208 is connected with the rear side of the conveying plunger 206 and the rear side of the monomer receptacle 202 in a gas-permeable manner via a compressed gas line 266. With the compressed gas connection 208 and via the compressed gas line 266, a compressed gas cartridge 210 can be connected to the interior chamber of the monomer receptacle 202 as a compressed gas source, so that a compressed gas can flow from the compressed gas cartridge 210 behind the conveying plunger 206 into the interior chamber of the monomer receptacle 202 and drive forward the conveying plunger 206 by the gas pressure in the direction of a cartridge head 260 and the cartridge 201.

The delivery plunger 207 has a hollow cylinder 209 on its front side to extend the distance that the monomer liquid 204 must flow through the cement powder 205, until it reaches the interior wall of the cartridge 201. Additionally, the hollow cylinder 209 is used to separate the delivery plunger 207 from a delivery opening on the front side of the interior chamber of the cartridge 201 and to create a dead volume between the delivery plunger 207 and the front side of the interior chamber of the cartridge 201 when the delivery plunger 207 or the hollow cylinder 209 is pressed to the maximum degree onto the front side of the interior chamber of the cartridge 201. The hollow cylinder 209 is here formed in a rotationally symmetric manner and in the style of a slit tube piece. For this purpose, the hollow cylinder 209 has longitudinal cuts that run parallel to the cylinder axis of the hollow cylinder 209.

In the interior chamber of the monomer receptacle 202, a bearing 212 made of foam is provided which serves to provide security during transportation and as a shock absorber for the glass ampoule 203. In this manner, it is to be prevented that the glass ampoule 203 breaks open in an unwanted manner during shock or impact.

The cartridge 201 and the monomer receptacle 202 are designed as a separate plastic parts arranged adjacent to each other. The monomer receptacle 202 and the cartridge are connected with each other in a manner that is liquid permeable for the monomer liquid 204 via the connection 214 in the delivery plunger 207, the line and an opening in the side wall of the cartridge 201. The connection 214 opens up in the delivery plunger 207 into the interior chamber of the cartridge 201 through a porous filter 216 that is impermeable for the cement powder 205 but permeable for the monomer liquid 204.

In the confluence to the connection 214, a filter 218 is arranged in the delivery plunger 207 with which the splinters 252 of the glass ampoule 203 can be retained. Instead of the filter 218 or in addition to the filter 218, a screen can also be provided.

The cylindrical conveying plunger 206 has an external circumference that matches the cylinder geometry of the interior chamber of the monomer receptacle 202 and is sealed against the interior wall of the monomer receptacle 202 in a liquid-tight and pressure-tight manner via two circumferential seals 226. Equally, the insert of the confluence of the compressed gas line 266 is sealed in a pressure-tight manner against the interior wall of the monomer receptacle 202 via the two external circumferential seals 227. Further, the delivery plunger 207 is sealed against the interior wall of the cartridge 201 in the liquid-tight manner via two circumferential seals 228. The seals 226, 227 serve to ensure that the gas pressure cannot escape from the compressed gas cartridge 210 and is available for driving forward the conveying plunger 206. The seals 228 serve to prevent an exit of monomer liquid 204 or of bone cement paste 254 in order to prevent contamination of the environment (of the operating theater and the user). The seals 226, 227, 228 can here consist of rubber.

On the front side of the cartridge 201, a connection 234 is provided in the form of an outer thread, onto which the cartridge head 260 is screwed as a completion of the cartridge 201. In the cartridge head 260, the delivery opening is formed and in the initial state (see the FIGS. 12 and 13) is closed with a closure 236 which is inserted in the delivery opening and closes said opening. The closure 236 is first opened to deliver the mixed bone cement paste 254 (see FIG. 14B and FIG. 15A). The closure 236 is a porous filter that is impermeable for the cement powder 205 but permeable for gases and has a cylindrical form. The closure 236 is preferably made of Porex or another open-pored plastic.

On the outer thread 234 on the front side of the cartridge 201, the cartridge head 260 is screwed, which comprises a line element 237 with a closure holder 238 for holding the closure 236. The closure holder 238 is formed according to a type of sleeve and has four bars 239 aligned in the longitudinal direction and rising into the closure holder 238. The bars 239 distance the closure 236 from the interior wall of the closure holder 238 when the closure 236 is pressed into the closure holder 238. In front of the closure holder 238, the line element tapers 237. In this area, four further bars 240 are arranged which form a stop 240 for the movement of the closure 236 and thus limit the movement of the closure 236 into the closure holder 238. Between the bars 239, 240, a sufficiently free line cross-selection is provided, so that a bone cement paste 254 produced from the parent components 204, 205 (see FIGS. 13, 14B, and 15A) can flow between the bars 239, the wall of the closure holder 238 and the inserted closure 236, as well as between the bars 239, the wall of the closure holder 238 and the inserted closure 236, as well as between the bars 240 in the front portion of the line element 237.

On the front side of the cartridge head 260, a tube 262 is connected which ends in a Luer lock adapter 268 and through which the bone cement paste 254 can be filled or be forwarded to a kyphoplasty system (not shown) or a spine applicator (not shown), which can be connected to the Luer lock adapter 268.

In the housing 264, a container 241 is provided for the compressed gas cartridge 210, which can also be produced as a plastic part using injection moulding, and which is arranged parallel to the cartridge 201 and the monomer receptacle 202 in the housing 264. The container 241 comprises the compressed gas connection 208 on its front side which faces towards the compressed gas line 266. The compressed gas cartridge 210 is inserted from the rear side into the container 241 for the compressed gas cartridge 210 and the container 241 is closed with a lid on the rear side.

Through the closure 236 which is designed as a porous filter, the interior of the cartridge 201 and the cement powder 205 can be sterilised with the aid of ethylene oxide, since the line element 237 is open and the closure 236 and the intermediate spaces between the powder particles of the cement powder 205 are permeable to air. At the same time, air can be pressed out of the monomer receptacle 202 through the connection 214, the cement powder 205, the closure 236 and the open line element 237, when the conveying plunger 206 is pressed in the direction of the monomer receptacle 202.

The cement powder 205 is enclosed in the cartridge 201, since all openings and connections 214 are impermeably closed for the cement powder 205 with the aid of the porous filters 216, 236. The content of the cartridge 201 can here by sterilised through evacuation and rinsing with ethylene oxide. As a result, the device is also suitable for the long-term storage of the cement powder 205.

The compressed gas connection 208 has a hollow needle 243 with which the compressed gas cartridge 210 is to be opened when this is pushed onto the hollow needle 243 with a membrane on its front side. Then the compressed gas 211 flows from the compressed gas cartridge 210 through the hollow needle 243, the compressed gas line 266 and a sterile filter in the compressed gas line 266 into the interior chamber of the monomer receptacle 202 behind the conveying plunger 206.

The compressed gas cartridge 210 can be opened, whereby a wing screw head 248 is turned, which extends through a passage in the rear lid of the container 241 for the compressed gas cartridge 210 and is affixed on the floor of the compressed gas cartridge 210. The compressed gas cartridge 210 has an outer thread on its front side facing towards the hollow needle 243, and the compressed gas connection 208 has a matching inner thread. With the wing screw head 248, the compressed gas cartridge 210 within the container 241 can be screwed deeper into the compressed gas connection 208 towards the front, so that the membrane on the front side of the compressed gas cartridge 210 is pierced by the hollow needle 243 and the compressed gas 211 is available within the device (see FIG. 14A).

Due to the pressure acting on the rear side of the conveying plunger 206, the conveying plunger 206 is pressed in the direction of the cartridge head 260 and the glass ampoule 203 is splintered between the conveying plunger 206 and the delivery plunger 207 and is opened as a result. The splinters 252 of the glass ampoule 203 are further compressed and the released monomer liquid 204 is pressed through the filter 218, through the connections 214 and through the porous filter 216 into the interior chamber of the cartridge 201 and thus into the cement powder 205. The delivery plunger 207 is here held by the cement powder 205, since the cement powder 205 is not flowable in a dry state. In the interior chamber of the cartridge 201, the monomer liquid 204 mixes with the cement powder 205, since in the cement powder 205 an additive is distributed which guides the monomer liquid 204 and thus distributes it In the cement powder 205 before the monomer liquid 204 reacts with the cement powder 205 and swells up such that a further dissemination of the monomer liquid 204 is prevented. In addition, the monomer liquid 204 can penetrate deep into the cement powder 205 along the hollow cylinder 209. In the interior chamber of the cartridge 201, the bone cement paste 254 is thus formed (see FIG. 14B).

The bone cement paste 254 produced with the device can be filled with the device into a syringe (not shown) with which the bone cement paste 254 can be applied by the user (the operator) on the patient. Alternatively, the bone cement paste 254 can be applied via an application system which is connected to the Luer lock adapter 268.

In order to render the device pressure-free, a branch is provided in the compressed gas line 266, which leads to a pressure release valve 276 which can be operated from outside with a valve handle 270. When the monomer liquid 204 has been pressed into the cartridge 201, the pressure release valve 276 can be opened and the compressed gas 211 can be blown out. As a result, the device becomes pressure-free and can be re-used and then disposed of without risk.

In a closed state, the closure 236 is arranged in an insert 258 on the cartridge head 260, which protrudes at the front into the interior chamber of the cartridge 201 and which is sealed with two circumferential seals 259 against the interior wall of the cartridge 201. The inserted 258 here forms a stop for the hollow cylinder 209 on the front side of the delivery plunger 207 and thus for the delivery plunger 207.

FIGS. 13, 14A to 14B, and 15A to 15B show five schematic profile views of the one embodiment of the device according to the invention to clearly illustrate the procedure of a method according to the invention. In addition, FIGS. 11 and 12 show an external view and a partial cross-section view of the device in the initial state. At the start of the method, the device is in the initial state, as shown FIG. 13. In this state, the device is sterilised.

Figure 14A:
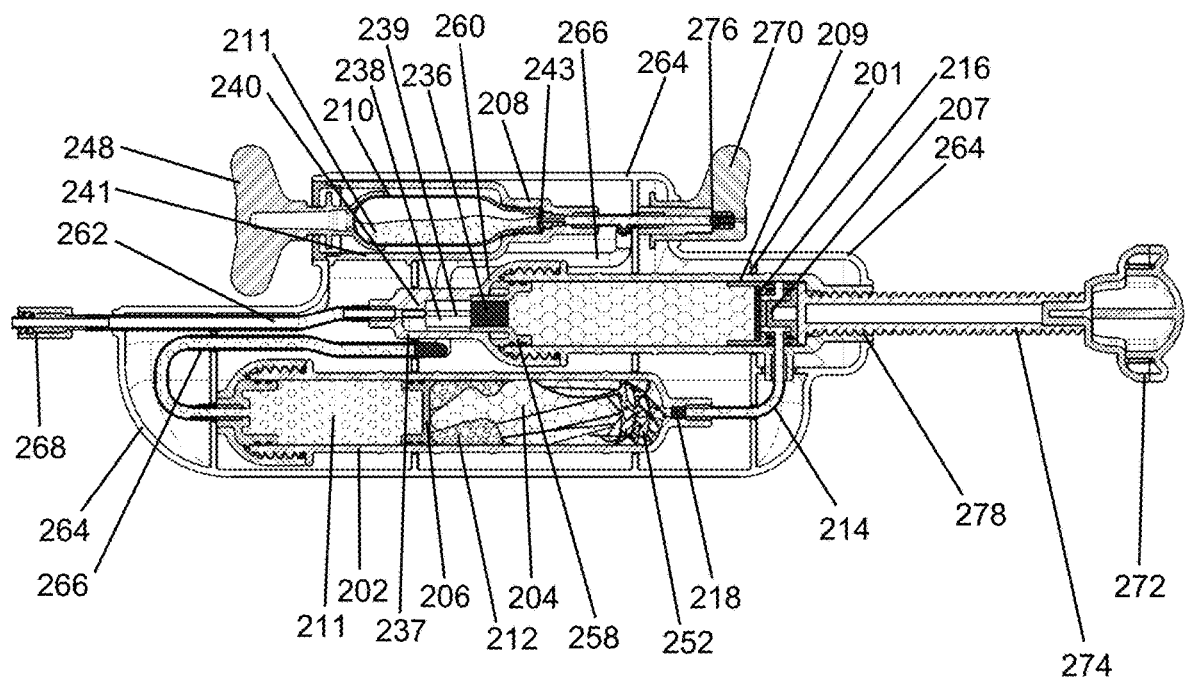
FIGS. 14A and 14B: show two schematic profile views of the third device according to the invention according to FIGS. 11 to 13 over each other to clearly illustrate the procedure of a method according to the invention.

Then, the compressed gas cartridge 210 is opened whereby the compressed gas cartridge 210 is screwed onto the hollow needle 243 with the wing head screw 248. This situation is shown in FIG. 14A.

Then, the main part of the method according to the invention begins.

The compressed gas 211 exiting from the compressed gas cartridge 210 flows through the compressed gas line 266 and through the sterile filter and presses onto the conveying plunger 206, pressing it forward towards the connection 214. Through the compressed gas 211 that continues to flow from the compressed gas cartridge 210 into the rear interior chamber of the monomer receptacle 202, the conveying plunger 206 is driven forward towards the connection 214. The bearing 212 is compressed and the conveying plunger 206 impacts on the head of the glass ampoule 203. Since the glass ampoule 203 lies on the front side on the monomer receptacle 202, and the interior chamber of the monomer receptacle 202 further decreases in size, the glass ampoule 203 is broken. The monomer liquid 204 exits from the glass ampoule 203 into the interior chamber of the monomer receptacle 2020. Remaining air from the monomer receptacle 202 is pushed out through the filter 218, the connection 214, the porous filter 216, through the intermediate spaces between the particles of the cement powder 205, through the closure 236 and from the line element 237 out of the device.

Only small splinters 252 are ultimately left from the glass ampoule 203, which are retained by the filter 218 and which remain in the monomer receptacle 202. The monomer liquid 204 is pressed through the filter 218, the connection 214 and the porous filter 216 into the cement powder 205 and there beings to react with the cement powder 205 so that the bone cement paste 254 is formed from the mixture. Here, the monomer liquid 204 cannot directly flow from the porous filter 216 to the interior wall of the cartridge 201, since this is covered by the slit hollow cylinder 209. As a result, the monomer liquid 204 is forced to forge a path through the cement powder 205. Monomer liquid bubbles or monomer liquid accumulations can thus be prevented.

Figure 14B:
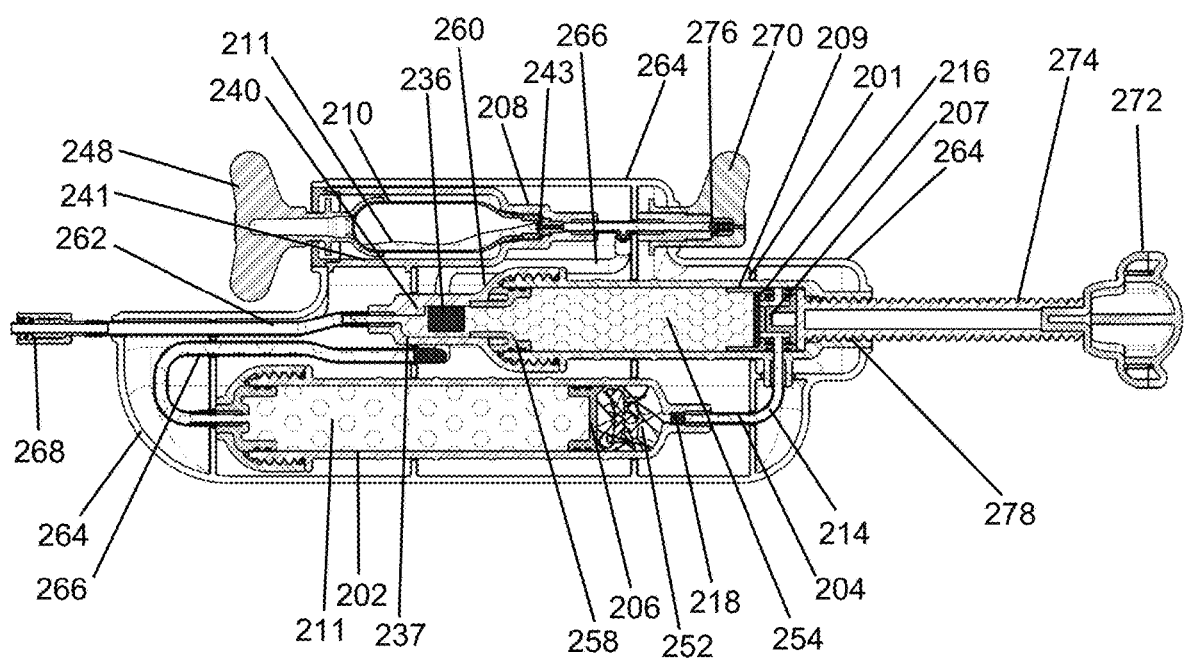

The quantity of monomer liquid 204 is selected such that the cement powder 205 (FIG. 13) is moistened with the monomer liquid 204 up until the foremost tip of the cartridge 201, i.e. up until closure 236 (see FIG. 14B).

Then, the bone cement paste 254 can be driven out of the cartridge 201 through driving forward of the delivery plunger 207 from the cartridge 201 and the tube 262. For this purpose, a threaded rod 274 is provided, which can be operated from the outside with a rotary handle 272. In the rear side of the cartridge 201, an inner thread 278 is provided for this purpose in which the threaded rod 274 can be screwed. Through the screwing in of the threaded rod 274, the delivery plunger 207 is driven towards the cartridge head 260. Here, the side opening in the wall of the cartridge 201 is closed by the delivery plunger 207 driven forward and the seals 228.

The closure 236 is driven forwards onto the delivery plunger 207 by the pressure acting on the bone cement paste 254 due to the threaded rod 274 and is pressed into the closure holder 238, until the closure 236 hits the stop 240, where the movement of the closure 236 ends. The bone cement paste 254 flows around the closure 236, whereby it flows through between the bars 239 and between the bars 240. Finally the bone cement paste 254 exits on the front side of the device through the tube 262.

Figure 15A:
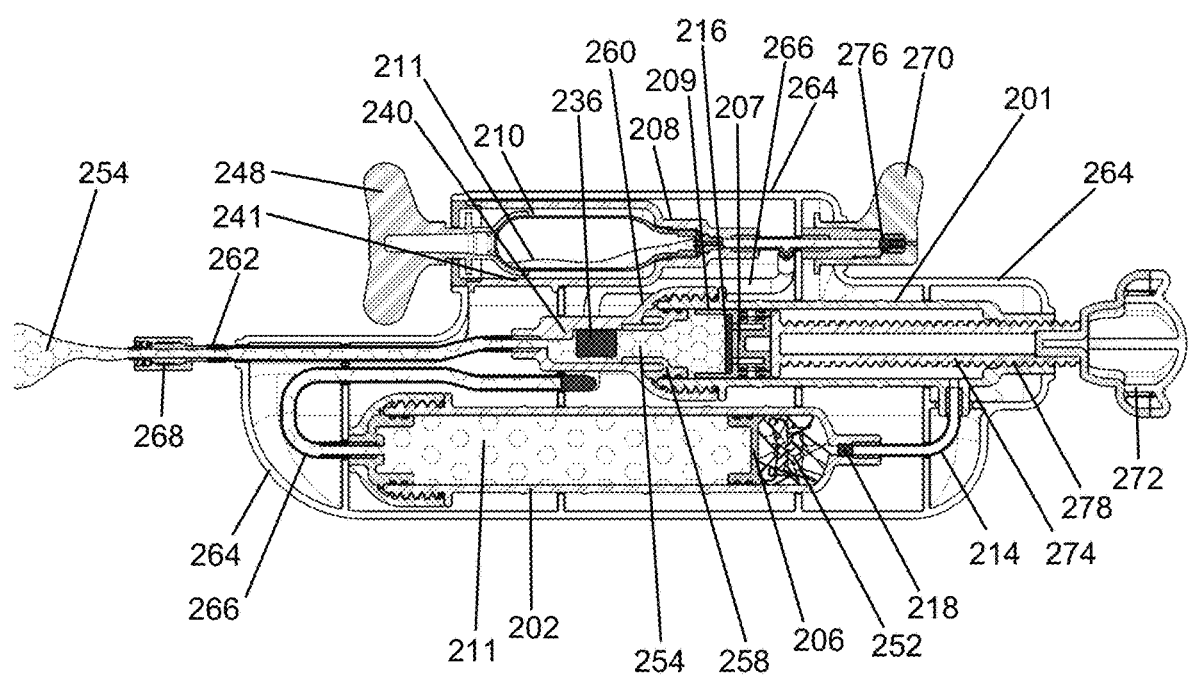
FIGS. 15A and 15B: show further schematic profile views of the third device according to the invention according to FIGS. 11 to 13 and 14A and 14B over each other to clearly illustrate the further procedure of a method according to the invention.

Through further driving forward of the delivery plunger 207 with the threaded rod 274, the bone cement past 254 is driven out of the cartridge 201. This situation is shown in FIG. 15A.

Figure 15B:
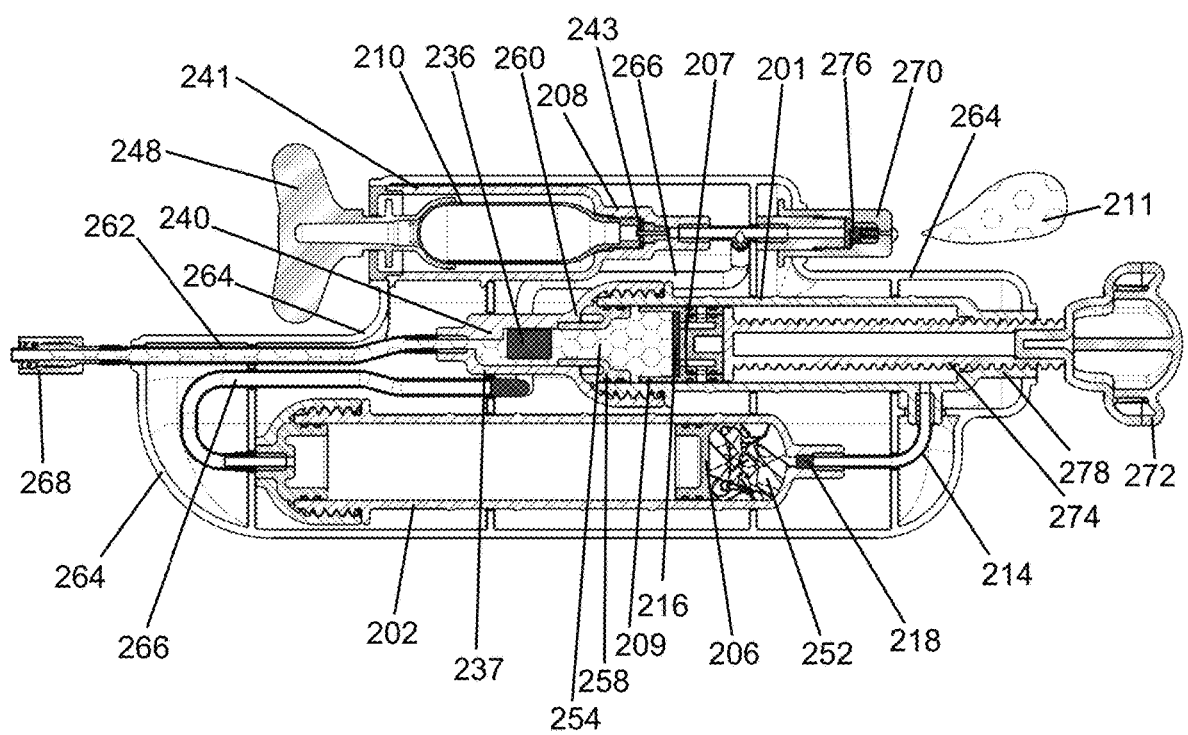

Finally the hollow cylinder 209 impacts the cartridge head 260 or the insert 258 in the cartridge head 260 on the front side of the interior chamber of the cartridge 201. Then, the pressure release valve 276 is opened with the valve handle 270 and the compressed gas 211 is blown out of the device. This situation is shown in FIG. 15B.

The hollow cylinder 209 has a height of 3 mm, preferably of 5 mm or greater, so that through the distance generated by it, it is guaranteed that the front side of the delivery plunger 207 is at a distance from the front side of the interior chamber of the cartridge 201, when the delivery plunger 207 is pressed forwards as far as possible. As a result, in the interior chamber of the cartridge 201, in the area delimited by the hollow cylinder 209, a dead volume is created which cannot be driven out of the cartridge 201 through the delivery opening, the line element 237 and the tube 262.

In this dead volume, a portion of the bone cement paste 254 is now located, which possibly contains too great a proportion of monomer liquid 204. This portion of bone cement paste 254 cannot be pressed out of the dead volume out of the device. Through this construction, it is ensured that no bone cement paste 254 can be applied with the device with a changing consistency due to the changing composition.

The third embodiment according to FIGS. 11 to 13, 14A to 14B, and 15A to 15B mainly differs from the first embodiment according to FIGS. 1A to 1E, 2, and 3A to 3B in that the compressed gas connection 208 is not directly placed on the monomer receptacle 202, and from the first two designs according to FIGS. 1A to 1E, 2, 3A to 3B, 4 to 9, and 10A to 10B by the fact that the cartridge 201 and the monomer receptacle 202 do not form a shared container, but like the container 241 are arranged parallel to each other in the shared housing 264.

The third embodiment can be used together with a so-called spine applicator for spondylosis or with a kyphoplasty system, whereby the kyphoplasty system or the spine applicator is connected to the Luer lock adapter 268. The spine applicator or the kyphoplasty system is used to block or rigidify two vertebrae or to fill hollow spaces in the vertebrae, whereby the bone cement paste 254 is applied with the aid of a trocar (not shown) in the area of the vertebrae under X-ray monitoring. Due to the trocar, the doctor does not have to work in the area of the radiation.

In a further alternative fourth embodiment, the system comprises, according to the third embodiment shown in FIGS. 11 to 13, 14A to 14B, and 15A to 15B, a syringe 53 (FIG. 7) or a kyphoplasty system or a spine applicator as an additional component which is detachably connected to the device and which can be filled via the tube 262. After the bone cement paste 254 have been mixed and transferred via the tube 262 or the Luer lock adapter 268 into the additional component, this can be removed and the bone cement paste 254 can be used with this component.

The features of the invention disclosed in the above description, as well as in the claims, figures and exemplary embodiments, can be essential both individually and in any combination required for the realization of the invention in its different embodiments.

The invention claimed is:

1. A device for producing a bone cement paste from a monomer liquid and a cement powder as parent components of the bone cement paste, the device comprising:
   a cartridge with a cylindrical interior chamber for mixing the parent components, whereby the cylindrical interior chamber of the cartridge is closed on a front side up to a delivery opening for expelling the bone cement paste from the cylindrical interior chamber,
   a delivery plunger which is arranged in the cylindrical interior chamber of the cartridge and which is supported in a linearly movable manner in a direction of the delivery opening,
   the cement powder which is arranged in the cylindrical interior chamber of the cartridge between the delivery opening and the delivery plunger,
   a monomer receptacle with an interior chamber in which a monomer liquid container containing the monomer liquid is contained, whereby in the monomer receptacle a conveying plunger is arranged that is movable in the longitudinal direction of the monomer receptacle,
   a compressed gas connection which is directly connected or connected via a compressed gas line in a pressure-tight manner with the interior chamber of the monomer receptacle, whereby the conveying plunger is arranged between the monomer liquid container and the compressed gas connection or the compressed gas line in the monomer receptacle, and
   a connection which connects the interior chamber of the monomer receptacle and the cylindrical interior chamber of the cartridge which is permeable to the monomer liquid but impermeable to the cement powder, whereby the monomer liquid container is arranged between the conveying plunger and the connection, wherein a movement of the conveying plunger presses the monomer liquid through the connection into the cylindrical interior chamber of the cartridge.

2. The device according to claim 1, wherein the conveying plunger is adapted to be pressed with a gas pressure that is guided via the compressed gas connection into the interior chamber of the monomer receptacle in the direction of the connection, and the monomer liquid container is adapted to be opened by the movement of the conveying plunger.

3. The device according to claim 1, wherein the conveying plunger is impermeable to gases and is sealed in a gas-tight manner against the interior walls of the monomer receptacle with at least one circumferential seal.

4. The device according to claim 1, wherein the connection comprises at least one passage inside the delivery plunger whereby the at least one passage is permeable with regard to the monomer liquid and gases, and is impermeable with regard to the cement powder, and the surface of the delivery plunger is impermeable with regard to the cement powder.

5. The device according to claim 1, wherein the monomer liquid container, containing the monomer liquid, is arranged between the conveying plunger and the delivery plunger.

6. The device according to claim 1, wherein the device has a compressed gas cartridge which is connected or adapted to be connect in a pressure-tight manner to the compressed gas connection, whereby the compressed gas cartridge is a $CO_2$ cartridge.

7. The device according to claim 1, wherein the compressed gas connection comprises a valve or an opening device, whereby the opening device is adapted to open a closed compressed gas cartridge and produce a pressure-tight connection between the compressed gas connection and the compressed gas cartridge, and whereby the compressed gas cartridge and the opening device are supported in the device such that they are adapted to contact each other and the compressed gas cartridge is adapted to be opened in the device through the pushing together of the compressed gas cartridge and the opening device, so that compressed gas flows from the compressed gas cartridge into the interior chamber of the monomer receptacle.

8. The device according to claim 1, wherein the device further has a container for a compressed gas cartridge, whereby a compressed gas cartridge inserted into the container is adapted to be opened in the device by a movement of the compressed gas cartridge against the compressed gas connection such that the compressed gas flows out of the compressed gas cartridge into the compressed gas connection.

9. The device according to claim 1, wherein a discharge valve is located in the compressed gas connection or in the compressed gas line.

10. The device according to claim 1, wherein between the connection and the monomer liquid container, an elastically deformable spacer is arranged and separates the monomer liquid container from the connection by at least 3 mm.

11. The device according to claim 1, wherein an additive conducting the monomer liquid is distributed in the cement powder.

12. The device according to claim 1, wherein the cylindrical interior chamber of the cartridge and the interior chamber of the monomer receptacle form a shared cylindrical interior chamber and align with each other, so that the delivery plunger is adapted to be driven forward with the conveying plunger in the cylindrical interior chamber of the cartridge and the delivery plunger adapted to be pressed into the cylindrical interior chamber of the cartridge.

13. The device according to claim 1, wherein on the compressed gas connection or in the compressed gas line a closed overpressure valve is arranged which is adapted to open the compressed gas connection or the compressed gas line to the environment when a threshold pressure is exceeded.

14. The device according to claim 1, wherein a rear side of the cartridge is connected with a front side of the monomer receptacle such that the cylindrical interior chamber of the cartridge aligns with the interior chamber of the monomer receptacle.

15. The device according to claim 1, wherein a ventilation opening is provided in the compressed gas connection or in the monomer receptacle, whereby the ventilation opening is adapted to be closed through a movement of the compressed gas connection or through a movement of a container for a compressed gas cartridge.

16. The device according to claim 1, wherein, on a front side of the delivery plunger facing towards the delivery opening, a hollow cylinder is arranged, whereby the hollow cylinder is open on its front side facing towards the delivery opening and the hollow cylinder extends from the front side of the delivery plunger at least 3 mm into the cylindrical interior chamber of the cartridge.

17. The device according to claim 1, wherein
the cement powder rests against the full surface of the front side of the delivery plunger.

\* \* \* \* \*